(12) United States Patent
Siniaguine

(10) Patent No.: US 8,247,634 B2
(45) Date of Patent: Aug. 21, 2012

(54) EXPANSION UNITS FOR ATTACHMENT TO CUSTOM PATTERNED WOUND DRESSINGS AND CUSTOM PATTERNED WOUND DRESSINGS ADAPTED TO INTERFACE WITH SAME

(75) Inventor: Oleg Siniaguine, San Carlos, CA (US)

(73) Assignee: PolyRemedy, Inc., San Jose, CA (US)

( * ) Notice: Subject to any disclaimer, the term of this patent is extended or adjusted under 35 U.S.C. 154(b) by 734 days.

(21) Appl. No.: 12/196,908

(22) Filed: Aug. 22, 2008

(65) Prior Publication Data

US 2010/0049148 A1 Feb. 25, 2010

(51) Int. Cl.
*A61F 13/00* (2006.01)
(52) U.S. Cl. ............................... 602/41; 602/42; 602/47
(58) Field of Classification Search ............ 602/42, 602/44, 45–46, 48, 52, 58, 41
See application file for complete search history.

(56) References Cited

U.S. PATENT DOCUMENTS

| | | | |
|---|---|---|---|
| 2,682,873 A | 7/1954 | Idnis | |
| 2,836,178 A | 5/1958 | Barr | |
| 3,140,572 A | 7/1964 | Petersen et al. | |
| 3,425,412 A | 2/1969 | Pope | |
| 3,729,892 A | 5/1973 | Aslund et al. | |
| 3,811,445 A | 5/1974 | Dostal | |
| 4,347,841 A | 9/1982 | Benyo et al. | |
| 4,522,203 A | 6/1985 | Mays | |
| 4,630,426 A | 12/1986 | Gentry | |
| 4,751,133 A | 6/1988 | Szycher et al. | |
| 4,869,936 A | 9/1989 | Moskowitz et al. | |
| 4,917,688 A | 4/1990 | Nelson et al. | |
| 4,948,540 A | 8/1990 | Nigam | |
| 4,957,795 A | 9/1990 | Riedel | |
| 5,000,172 A | 3/1991 | Ward | |
| 5,265,605 A | 11/1993 | Afflerbach | |
| 5,340,363 A | 8/1994 | Fabo | |
| 5,395,305 A | 3/1995 | Koide et al. | |
| 5,489,437 A | 2/1996 | Marra | |
| 5,520,735 A | 5/1996 | Mulder | |
| 5,520,762 A | 5/1996 | Rasmussen et al. | |
| 5,588,428 A | 12/1996 | Smith et al. | |

(Continued)

FOREIGN PATENT DOCUMENTS

EP 0509703 B1 10/1992

(Continued)

OTHER PUBLICATIONS

United States Office Action, U.S. Appl. No. 11/972,452, Jun. 14, 2011, 7 pages.

(Continued)

*Primary Examiner* — Michael A. Brown
(74) *Attorney, Agent, or Firm* — Fenwick & West LLP

(57) ABSTRACT

A custom fabricated (e.g. custom shaped and dimensioned) primary wound dressing part that matches a corresponding, pre-mapped integumentary wound is combined with dressing extension parts to form a composite wound dressing system. The primary wound dressing part may include one or more liquid flow barriers composed for example of a hydrophobic and high viscosity liquid embedded in a layer of the primary wound dressing part. The dressing extension parts may include interconnect portals for operatively interconnecting with the primary wound dressing part so that liquids may be securely moved between primary wound dressing part and the extension parts.

56 Claims, 7 Drawing Sheets

U.S. PATENT DOCUMENTS

| | | | |
|---|---|---|---|
| 5,641,501 | A | 6/1997 | Cooper et al. |
| 5,653,699 | A | 8/1997 | Reed et al. |
| 5,741,509 | A | 4/1998 | Kushner |
| 5,757,498 | A | 5/1998 | Klein, II et al. |
| 5,762,620 | A | 6/1998 | Cartmell et al. |
| 5,785,697 | A | 7/1998 | Trombetta et al. |
| 5,891,078 | A | 4/1999 | Turngren et al. |
| 5,899,871 | A | 5/1999 | Cartmell et al. |
| 5,935,363 | A | 8/1999 | Gilman et al. |
| 6,004,253 | A | 12/1999 | Riedel et al. |
| 6,043,408 | A | 3/2000 | Geng |
| 6,051,747 | A | 4/2000 | Lindqvist et al. |
| 6,062,285 | A | 5/2000 | Dotta et al. |
| 6,071,267 | A * | 6/2000 | Zamierowski ............... 604/289 |
| 6,153,215 | A | 11/2000 | Samuelsen et al. |
| 6,245,960 | B1 | 6/2001 | Eaton |
| 6,284,941 | B1 | 9/2001 | Cox et al. |
| 6,297,420 | B1 | 10/2001 | Heincke |
| 6,313,369 | B1 | 11/2001 | Schiraldi et al. |
| 6,420,622 | B1 | 7/2002 | Johnston et al. |
| 6,512,160 | B1 | 1/2003 | Rutsky |
| 6,520,425 | B1 | 2/2003 | Reneker |
| 6,655,112 | B1 | 12/2003 | Cremer et al. |
| 6,662,051 | B1 | 12/2003 | Eraker et al. |
| 6,753,454 | B1 | 6/2004 | Smith et al. |
| 6,765,123 | B2 | 7/2004 | de Jong et al. |
| 6,787,682 | B2 | 9/2004 | Gilman |
| 6,967,261 | B1 | 11/2005 | Soerens et al. |
| 7,105,058 | B1 | 9/2006 | Sinyagin |
| 5,681,579 | A1 | 10/2007 | Freeman |
| 7,347,846 | B2 | 3/2008 | Hermansson et al. |
| 2001/0000795 | A1 | 5/2001 | Bolian, II et al. |
| 2001/0003148 | A1 | 6/2001 | Coffee |
| 2002/0062097 | A1 | 5/2002 | Simpson |
| 2002/0133502 | A1 | 9/2002 | Rosenthal et al. |
| 2003/0050794 | A1 | 3/2003 | Keck |
| 2003/0233101 | A1 | 12/2003 | Lubock et al. |
| 2004/0015115 | A1* | 1/2004 | Sinyagin ............... 602/42 |
| 2004/0059199 | A1 | 3/2004 | Thomas et al. |
| 2004/0133143 | A1 | 7/2004 | Burton et al. |
| 2004/0167456 | A1 | 8/2004 | Kingsford et al. |
| 2005/0149259 | A1 | 7/2005 | Cherveny et al. |
| 2006/0020235 | A1 | 1/2006 | Siniaguine |
| 2006/0034816 | A1 | 2/2006 | Davis et al. |
| 2007/0118096 | A1 | 5/2007 | Smith et al. |
| 2007/0204691 | A1 | 9/2007 | Bogner et al. |
| 2007/0207688 | A1 | 9/2007 | Rasor |
| 2007/0237812 | A1 | 10/2007 | Patel et al. |
| 2008/0004904 | A1 | 1/2008 | Tran |
| 2008/0051688 | A1 | 2/2008 | Lowe |
| 2008/0077091 | A1 | 3/2008 | Mulligan |
| 2008/0108923 | A1 | 5/2008 | Sinyagin |
| 2008/0108927 | A1 | 5/2008 | Sinyagin |
| 2008/0167594 | A1 | 7/2008 | Siniaguine |
| 2008/0234618 | A1 | 9/2008 | Baldock |
| 2009/0024067 | A1 | 1/2009 | Siniaguine |
| 2009/0037224 | A1 | 2/2009 | Raduchel |
| 2009/0131825 | A1 | 5/2009 | Burbank et al. |
| 2009/0204423 | A1 | 8/2009 | Degheest et al. |
| 2009/0216553 | A1 | 8/2009 | Cellura |
| 2009/0245603 | A1 | 10/2009 | Koruga et al. |
| 2010/0114256 | A1 | 5/2010 | Chan et al. |
| 2010/0219546 | A1 | 9/2010 | Puttler et al. |

FOREIGN PATENT DOCUMENTS

| | | |
|---|---|---|
| WO | WO 97/42917 A1 | 11/1997 |
| WO | WO 00/43046 A2 | 7/2000 |

OTHER PUBLICATIONS

United States Office Action, U.S. Appl. No. 12/198,676, May 13, 2011, 8 pages.
PCT International Search Report and Written Opinion, PCT/US2010/031912, Jun. 18, 2010, 13 pages.
United States Office Action, U.S. Appl. No. 12/110,228, Jul. 28, 2011, 21 pages.
United States Office Action, U.S. Appl. No. 11/972,452, Jul. 28, 2011, 6 pages.
United States Office Action, U.S. Appl. No. 12/436,071, Aug. 24, 2011, 19 pages.
United States Office Action, U.S. Appl. No. 12/198,676, Sep. 6, 2011, 8 pages.
U.S. Appl. No. 60/840,412, filed Aug. 28, 2006, Lowe, 6 pages.
International Search Report, PCT/US09/039545, mailing date May 29, 2009.
Written Opinion of the International Searching Authority, PCT/US09/039545, Sep. 29, 2009.
European Search Report, EP 03 72 8787.7, dated May 24, 2006, 4 pages.
Examination Report of the European Patent Office, EP 03 72 8787.7, dated May 18, 2007, 7 pages.
International Search Report, PCT/US03/14574, mailing date Oct. 1, 2003.
PCT International Search Report and Written Opinion, PCT/US2009/048412, Oct. 13, 2009, 13 pages.
PCT International Search Report and Written Opinion, PCT/US2008/50762. Jun. 25, 2008, 10 pages.
PCT International Search Report and Written Opinion, PCT/US2005/25362, Sep. 1, 2006, 9 pages.
Siniaguine, O., "Automatic System for On-Demand Fabrication of Wound Dressings," 2007, pp. 1-15.
United States Office Action, U.S. Appl. No. 10/431,888, Aug. 17, 2009, 17 pages.
United States Office Action, U.S. Appl. No. 10/431,888, Jun. 23, 2009, 14 pages.
United States Office Action, U.S. Appl. No. 10/431,888, Nov. 25, 2008, 11 pages.
United States Office Action, U.S. Appl. No. 10/431,888, Dec. 11, 2007, 8 pages.
United States Office Action, U.S. Appl. No. 10/431,888, Apr. 10, 2007, 7 pages.
United States Office Action, U.S. Appl. No. 11/972,854, Feb. 2, 2010 14 pages.
United States Office Action, U.S. Appl. No. 11/972,854, Jun. 24, 2009, 8 pages.
United States Office Action, U.S. Appl. No. 11/972,846, Jan. 25, 2010, 12 pages.
United States Office Action, U.S. Appl. No. 11/972,846, Jun. 24, 2009, 8 pages.
United States Office Action, U.S. Appl. No. 12/198,604, Jan. 21, 2010, 30 pages.
United States Office Action, U.S. Appl. No. 12/198,604, Jun. 25, 2009, 12 pages.
United States Office Action, U.S. Appl. No. 12/198,676, Sep. 16, 2009, 8 pages.
United States Office Action, U.S. Appl. No. 11/183,459, May 9, 2008, 9 pages.
United States Office Action, U.S. Appl. No. 10/382,422, May 2, 2005, 16 pages.
U.S. Appl. No. 10/431,058, May 22, 2008.
U.S. Appl. No. 12/164,451, filed Jun. 30, 2008, Siniaguine.
U.S. Appl. No. 12/436,071, filed May 5, 2009, Siniaguine.
United States Office Action, U.S. Appl. No. 11/972,452, Nov. 10, 2011, 6 pages.
United States Office Action, U.S. Appl. No. 12/164,451, Oct. 13, 2011, 17 pages.
European Examination Report, European Application No. 03728787.7, Nov. 15, 2010, 6 pages.
European Extended Search Report, European Application No. 05773145.7, Jan. 4, 2011, 10 pages.
United States Office Action, U.S. Appl. No. 12/110,228, Oct. 22, 2010, 21 pages.
United States Office Action, U.S. Appl. No. 12/436,071, Oct. 22, 2010, 18 pages.
United States Office Action, U.S. Appl. No. 11/972,452, Dec. 3, 2010, 9 pages.
United States Office Action, U.S. Appl. No. 12/198,676, Jan. 19, 2011, 8 pages.
United States Office Action, U.S. Appl. No. 10/431,888, Jun. 10, 2010, 18 pages.

"IMPAC Introduces Comprehensive Cancer Outcomes Analytical Suites," Business Wire, published Mar. 7, 2000. Dialog, (File 610 Business Wire), Dialog ID No. 00210331.

"Iteration" Wikipedia, 3 pages, [Online] [Retrieved on Feb. 28, 2011] Retrieved from the Internet<URL:www.wikipedia.com>.

United States Office Action, U.S. Appl. No. 12/110,228, Mar. 7, 2011, 21 pages.

United States Office Action, U.S. Appl. No. 12/436,071, Apr. 1, 2011, 20 pages.

U.S. Appl. No. 11/183,459, filed Jul. 8, 2005, Oleg Siniaguine.

U.S. Appl. No. 12/198,604, filed Aug. 26, 2008, Oleg Siniaguine.

U.S. Appl. No. 12/198,676, filed Aug. 26, 2008, Oleg Siniaguine.

Canadian Examination Report, Canadian Application No. 2,524,934, Feb. 8, 2010, 3 pages.

European Examination Report, European Application No. 03728787.7, Feb. 26, 2010, 4 pages.

International Search Report and Written Opinion, PCT/US2009/054458, Oct. 9, 2009, 3 pages.

United States Office Action, U.S. Appl. No. 12/198,676, Mar. 12, 2010, 7 pages.

U.S. Appl. No. 10/431,888, filed May 7, 2003, Sinyagin.

U.S. Appl. No. 11/972,854, filed Jan. 11, 2008, Sinyagin.

U.S. Appl. No. 11/972,846, filed Jan. 11, 2008, Sinyagin.

U.S. Appl. No. 10/382,422, filed Mar. 5, 2003, Sinyagin.

U.S. Appl. No. 11/972,452, filed Jan. 10, 2008, Siniaguine.

U.S. Appl. No. 12/110,228, filed Apr. 25, 2008, DeGheest et al.

U.S. Appl. No. 12/436,071, filed May 5, 2009, Siniaguine et al.

European Examination Report, European Application No. 05773145.7, Jan. 17, 2012, 5 pages.

United States Office Action, U.S. Appl. No. 12/110,228, Jan. 31, 2012, 20 pages.

United States Office Action, U.S. Appl. No. 12/436,071, Feb. 13, 2012, 18 pages.

United States Office Action, U.S. Appl. No. 13/052,553, Mar. 20, 2012, 9 pages.

* cited by examiner

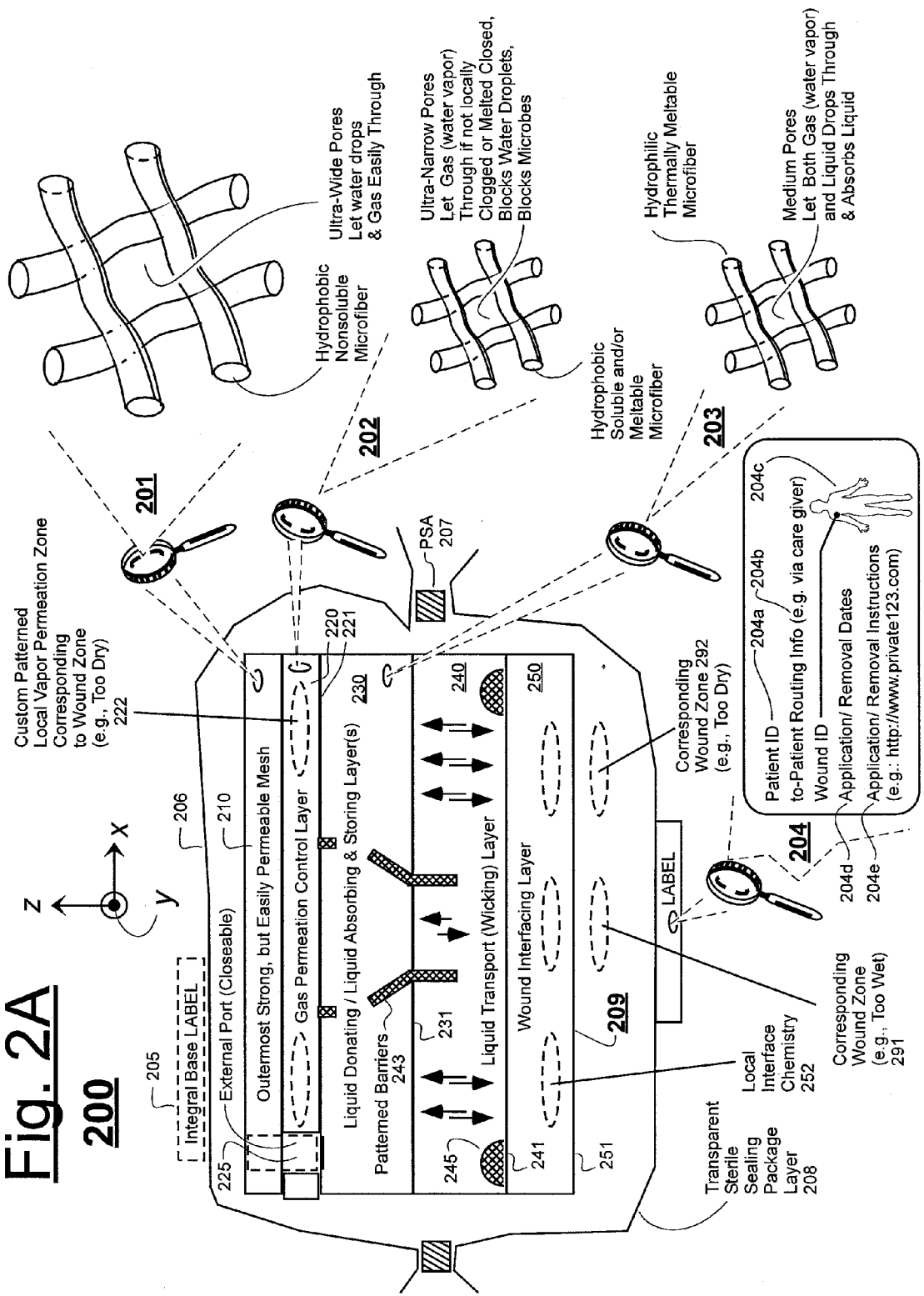

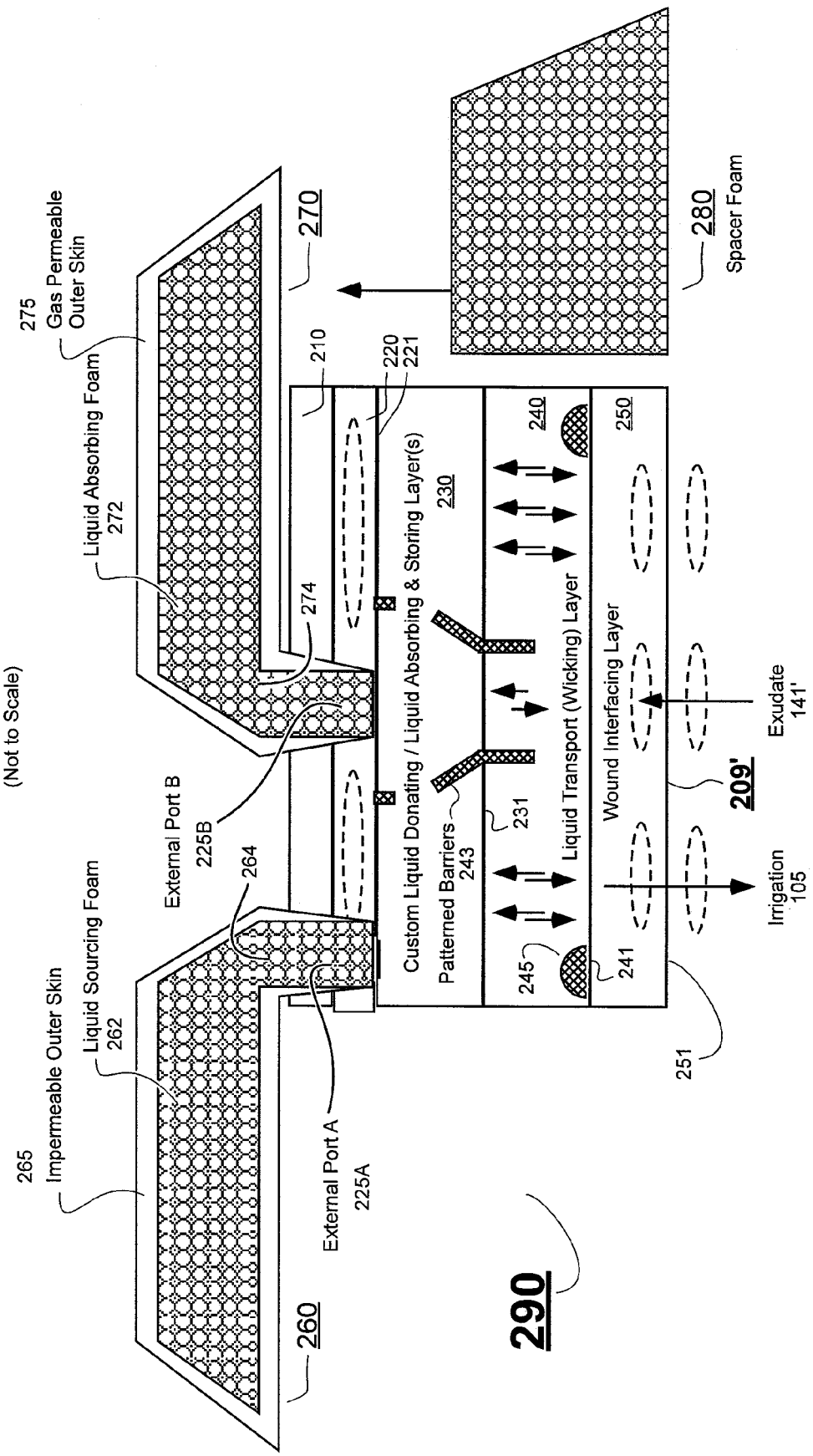

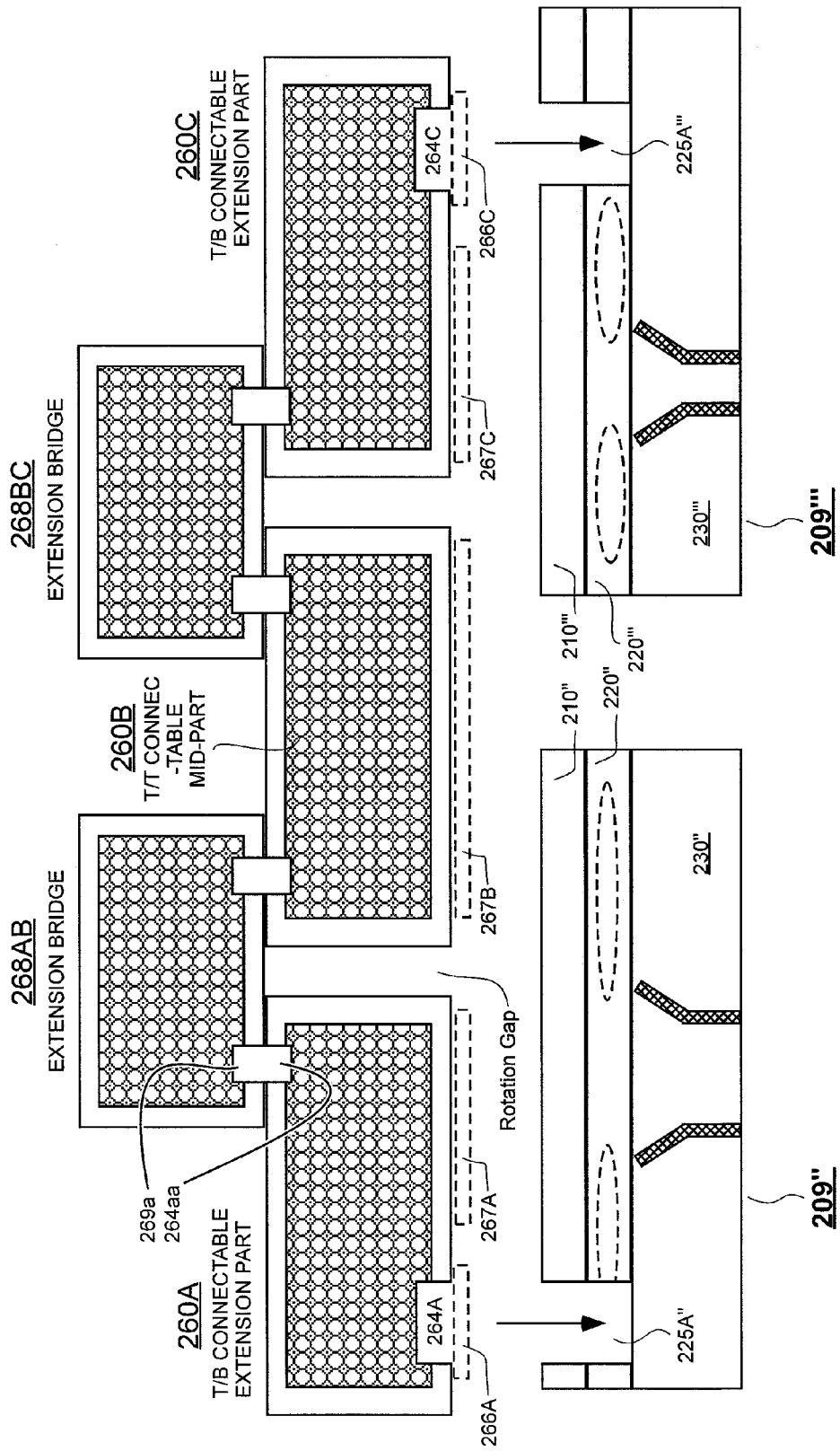

EXPANSION UNITS FOR ATTACHMENT TO CUSTOM PATTERNED WOUND DRESSINGS AND CUSTOM PATTERNED WOUND DRESSINGS ADAPTED TO INTERFACE WITH SAME

CROSS-REFERENCE TO AND INCORPORATION OF CO-OWNED APPLICATIONS

The following U.S. patent applications are owned by the owner of the present application, and their disclosures are incorporated herein by reference:

(A) U.S. Ser. No. 11/972,452 filed Jan. 10, 2008 by Oleg SINIAGUINE, originally entitled, Wound Dressing with Controllable Permeability", and claiming priority of and incorporating U.S. Provisional applications 60/884,321 filed Jan. 10, 2007 and 60/888,693 filed Feb. 7, 2007; and (B) U.S. Ser. No. 12/164,451 filed Jun. 30, 2008 by Oleg SINIAGUINE, originally entitled, Custom Patterned Wound Dressings Having Patterned Fluid Flow Barriers and Methods of Manufacturing and Using Same.

CROSS REFERENCE TO AND INCORPORATION OF PUBLISHED APPLICATIONS AND PATENTS

The disclosures of the following published U.S. patent applications or patents are incorporated herein by reference:

(A) U.S. Pat. No. 7,105,058, issued Sep. 12, 2006 to Dmitriy Sinyagin and entitled "Apparatus for Forming Microfiber Coating";

(B) U.S. Pat. Publication No. 2004-0015115 and its underlying source: U.S. Ser. No. 10/431,888 filed May 7, 2003 by Dmitriy Sinyagin, originally entitled, "Method for Treating Wound, Dressing for Use Therewith, and Apparatus and System for Fabricating Dressing", and claiming priority of and incorporating U.S. Provisional application 60/378,635 filed May 7, 2002; and (C) U.S. Pat. Publication No. 2006-0020235 and its underlying source: U.S. Ser. No. 11/183,459 filed Jul. 18, 2005 by Oleg Siniaguine, originally entitled, "Wound Dressing and Apparatus for Manufacturing", and claiming priority of and incorporating U.S. Provisional application 60/588,628 filed Jul. 16, 2004.

FIELD OF DISCLOSURE

The present disclosure of invention relates generally to care and management of wounds to the integumentary systems of humans or of other mammals. The disclosure relates more specifically to the fabrication and use of custom tailored wound dressings that are custom patterned to match individual needs of individual wound zones over time on individual patients and also to expansion modules that can be operatively coupled to the custom tailored wound dressings.

DESCRIPTION OF RELATED TECHNOLOGY

The outer protective system or integument of human and other mammalian bodies is a complex system that is typically comprised of growing, aging and dying or dead skin cells; of oil glands, sweat glands, hair and hair follicles, peripheral blood vessels (capillaries), nerve endings and other components. For land dwelling mammals, the integument serves as a protective interface between delicate internal organs and a generally dry, and often microbe populated (dirty) and abrasive ambient environment which is hostile to delicate internal organs that need to be kept moisturized, fed with oxygenated blood, kept free of harmful microorganisms and kept at healthy body temperatures.

Healthy skin is constantly generating new skin cells (epitheliating cells) and progressively converting these new skin cells into aging, drying and dying cells that push their way outwardly through the epidermis to interface with the generally dry, dirty and abrasive ambient environment. Aside from interfacing with the generally hostile external environment, healthy skin generally performs many other vital functions including that of regulating body temperature (e.g., by sweating), excreting waste products (e.g., salts) and providing sense of touch.

In order to continue to provide these various functions, different levels of the epidermis in the skin require correspondingly different ones of graduated micro-climates and different physiochemical micro-environments. These graduated and differentiated micro-environments range from that of a relatively dry, yet nonetheless oil lubricated one at the outer surface of the epidermis to a relatively wet, fluidic and flowing environment at deeper levels of the integument where the basal epidermis and deeper parts of the integument tend to be populated by blood vessels and growing, dividing cells and the like.

When a skin puncturing wound occurs, these graduated systems of differentiated micro-climates and physiochemical micro-environments are generally disrupted. Areas of skin that are normally relatively dry may become unduly wet due to large flows of liquids (e.g., exudates) that discharge from the wound center and move out uncontrollably over drier skin areas. On the other hand, deeper parts of the skin structure that are normally wet and free of harmful microorganisms may become unduly dry and infected with colonized bacteria due to exposure to open air and contaminants. The amount and/or rate of excessive drying or excessive moisturizing in a wound area can vary from wound to wound and from area to area within a given wound.

Conventional wound treatments apply a homogenous wound dressing (e.g., one made of woven cotton threads) over the entire wound area primarily for the purpose of keeping the wound clean, protecting it from external contaminants as well as direct physical trauma and perhaps soaking up some initial bleeding. Generally there are only few standardizes sizes and shapes of dressing (e.g., 3 by 3 inch square gauze) that come with the understanding that the standardized, noncustom size can handle a wide range of different wounds.

More recently, custom tailored wound dressings have been proposed for treating wounds individually and at different stages of their development. More specifically, individual wounds of individual patients are mapped, measured and characterized according to their localized zones. For example, digital images of the wounds, with size and location calibrations, are taken in a natural visible light range and/or by other means (e.g., polarized light, IR images, UV images, etc.). The wound zones are characterized by associating different identifiable areas of the imaged wound with different wound zone characteristics (e.g., overly wet zone, overly dry zone, rate of exudation, rate of drying, expected durations of continued exudation/drying, etc.). Individual or overlapping treatment goals are then assigned to each of differently characterized wound zones. Thereafter corresponding dressing functions are designated for each of the differently characterized wound zones and these dressing functions (e.g., heavy absorption of moisture, blocking of evaporation, etc.) are unified to define localized functions of a custom tailored dressing that is to be automatically fabricated for and according to the individual dimensions of the individual wound zones of a given individual patient. The above-cited U.S. patent applications (incorporated herein by reference) disclose various methods for automatically custom designing and custom fabricating individual dressings for individual wounds. (This technological background section, incidentally, is not to be construed as an admission about prior art. Various concepts provided in this section may be novel ones and thus not part of prior art.)

While it is desirable to custom size, custom shape and/or custom pattern the one or more dressing layers that will form the custom wound dressing which directly interfaces with the wound so that the customized dressing zones will correctly match with corresponding wound zones, the making of the entire wound treatment system out of only highly customized parts can be time consuming, unduly expensive and thus problematic. Some functions of a dressing may be carried out with semi-standardized or fully standardized parts as will be seen in the details provided below.

SUMMARY

In accordance with one aspect of the present disclosure, a complete wound treatment system is formed by combining fully customized layers or other customized parts with semi-standardized or fully standardized other parts (less customized parts). More specifically, upper layers of a composite dressing system that do not directly interface with uniquely shaped wound zones can be sized and shaped more crudely than lower layers of the dressing that do directly interface with uniquely shaped wound zones. The less customized upper parts are operatively coupled in accordance with the present disclosure to the more customized lower parts by way of interface ports provided in the more customized layers.

More specifically, in one embodiment interface or portal openings are custom cut through an upper gas permeation control layer of a customized assembly of custom patterned dressing layers so as to expose one or more underlying hydrophilic layers. Custom, semi-standardized or fully standardized extension parts are then provided for coupling with the interface portals and providing for communication of liquids between the extension parts and the custom part. In one embodiment, the extension parts include bulk foam or other hydrophilic porous interiors that provide additional volumes of irrigating liquids to, or absorb additional volumes of waste liquids (e.g., exudates) from the underlying custom patterned dressing layers. The term "porous" as used herein is to be broadly construed unless explicitly stated otherwise as covering its many customary meanings within the context of this disclosure including: (1) pertaining to a material that is full of pores, vessels, interstices or other structures (e.g., microfibers) which provide enhanced internal cavity volume and/or enhanced internal surface area; (2) pertaining to a material that can absorb fluids (liquids or gases) into its pores, vessels or onto its other internal structures; and (3) pertaining to a material into which and/or from which small sized particles can pass depending on pore, vessel or mesh dimensions within the porous material as well as depending on other attributes of the porous material including whether the porous material has hydrophobic or hydrophilic internal surfaces. More specifically, the term porous material is to be construed, unless explicitly stated otherwise, as at least covering solid foam materials that can absorb or store fluids and materials composed of intersecting microfibers which can form filter structures of specifiable average pore sizes and/or of can form liquid absorbing structures of specifiable liquid absorbing rates and/or capacities.

Methods for using the extension parts in combination with the highly customized wound dressing parts are also disclosed. Other aspects of the disclosure will become apparent from the below detailed description.

BRIEF DESCRIPTION OF THE DRAWINGS

The below detailed description section makes reference to the accompanying drawings, in which:

FIG. 2A is a schematic diagram illustrating a sterile-wise packaged, custom patterned dressing part structured in accordance with the present disclosure;

FIG. 2B is a schematic diagram illustrating how one or more extension parts may be linked to the custom dressing part of FIG. 2A;

FIG. 2C is a schematic diagram illustrating how extension parts may be linked to one another and/or to multiple custom parts so as to provide a variably expandable and locatable set of wound treating resources;

DETAILED DESCRIPTION

Figure 1:
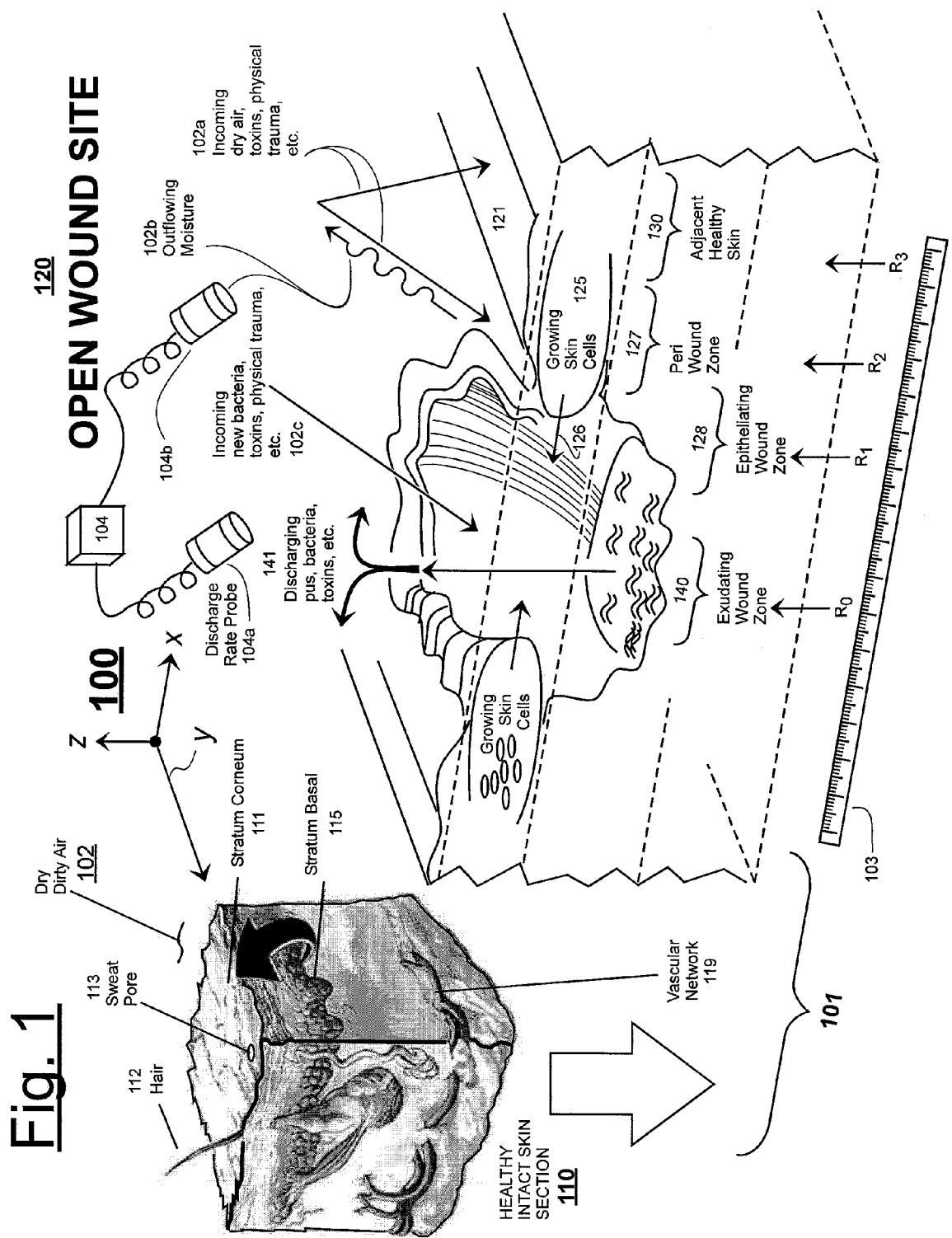
FIG. 1 is a perspective schematic showing a wound site that includes a block of healthy intact skin and an adjacent open wound.

FIG. 1 schematically represents a combination 100 of a given human living body 101 interacting with a potentially hostile external environment 102 (e.g., air contaminated with harmful microbes, with dirt, toxins, etc. and other surroundings which can inflict trauma on the body). Portion 110 of the body 101 represents a hypothetically sectionally removed cube of healthy skin tissue lying adjacent to an open wound in a wound site 120 also belonging to the given human patient 101. As seen, the healthy section 110 comprises a complex assortment of organelles and layers including a relatively dry and dead top portion 111 (stratum corneum) of the epidermis and a moderately wet, alive and reproducing basal portion 115 (stratum basal) of the epidermis.

Additionally, healthy and intact section 110 includes oil glands, hair follicles, hair 112, sweat pores 113, and a vascular network 119 positioned deeper within section 110. The vascular network 119 supplies oxygen, water and nutrients to the growing and reproducing cells of the basal portion 115 of the epidermis. It may be appreciated from FIG. 1A that the concentration of water in a healthy skin section such as 110 typically decreases as a continuum as one rises in the +Z (vertical) direction from the relatively wet environment of intact vascular network layer 119, through the epithelizing basal layer 115 and up to the aged and dry skin cells at the very top 111 of the epidermis. As is well known in the medical arts, dead skin cells are constantly flaking off in unnoticed quantities from the outermost part 111 of a healthy epidermis as the body 101 interacts abrasively with the outside environment 102 and new cells are constantly being generated by the intact and healthy basal layer 115 to replace the flaked off dermis.

Referring to the perspective schematic of the adjacent open wound site 120 in FIG. 1, it may be seen that once an open wound is created, the moderately moist, normal environment of the intact basal layer 115 is not present for exposed growing skin cells 125 that are trying to grow radially inward (in direction 126) to close up the wound opening. Instead these inward growth-attempting cells 125 are exposed to a much dryer and otherwise more hostile environment 102a due to the incoming dry air entering through the opening of wound site 120. During normal healing, epitheliating cells 125 grow laterally in a wound closing direction 126 from the still-intact surrounding skin (127 and/or 130) towards the center region, $R_O$ of the wound. At the same time, deeper vascular tissue (e.g., 119) tries to thrive and grow vertically upward in the +Z direction so as to restore the underlying support structure that nourishes the basal portion 115 of the epidermis in healthy intact skin (110). These various activities are desirable in order to close up the wound and permit quick healing.

Of course, many different mechanisms may be present to compete against and/or to block the radially inward healing process 126 attempted by peri-wound tissue (125, 127) and/or to thwart the upwardly moving (+Z) growth and restructuring processes attempted by the deeper tissue of the wound site 120. For example, the patient 101 may be afflicted with chronic diabetes, and/or with an impaired immune system, unusually dry skin, unusually oily skin, old age, and/or other medical conditions that prevent normal rapid healing. Aside from that, the open wound 120 may be exposed to dry and potentially dirty incoming air 102a as already mentioned. Secondly, one or more central regions (e.g., $R_O$) of the wound may have been infected by and thus colonized by harmful bacteria where that bacteria is causing damage to the subdermal tissue and impeding healing re-growth or even expanding the size of the wound due to expansion of the infection. The rate at which the colonizing bacteria grow may vary from patient to patient and wound to wound. Additionally or alternatively, new bacteria may enter the open wound site 120 from the outside environment 102b and thus infect it. When infections, external trauma or the like occur, the immune system and other aspects of the body try to go to work and to begin generating protective liquids in the process of fighting off invading microbes and/or filling up the open wound cavity. Some of the generated liquids (exudates) may be harmful to surrounding tissue such as surrounding healthy skin (e.g., to areas 121, 125, 127 and 130). Exudating liquids may include discharging pus, growing bacteria, and toxic chemicals generated in the exudating wound zone 140. If the surrounding tissue (121, 125, 127, 130) is harmed, it may not be able to contribute to the healing process (126) or worse yet, the exudated liquids may cause the wound site 120 to grow even larger.

Every human patient 101 is different and may have unique wound characteristics in terms of rates at which exudates are generated (e.g., milliliters per hour) and in terms of rates at which healing-promoting and thus needed moisture is lost to the ambient (e.g., also measured for example in micro or milliliters per hour). Every human patient 101 is usually also different in terms of the unique wound treatment prescribed for that patient including that of dictating the rate at which a clean flow of medications (or irrigating sterile solution) should be supplied into the wound site and the rate at which waste liquids (e.g., exudates) should be removed from the wound site.

Moreover, treatment facilities tend to differ from one another in terms of staffing and how often wound dressings can be changed and/or how complicated a dressing removal or application process can be. In some facilities it may be possible to change dressings every few hours under supervision of highly skilled staff whereas in others the best that can be hoped for is perhaps one change every 24 hours if not longer and only so long as the dressing replacement operation is simple enough for minimally skilled staff to understand. Such treatment attributes should be considered when a customized dressing is being designed. More specifically, if a certain first rate of exudate drainage (e.g., in terms of milliliters per hour) is desired and the dressing cannot be changed more often than once every 24 hours, then the exudate drainage absorption capacity of the dressing should be set to accommodate the first rate (projected exudate rate) in combination with the expected duration of 24 or more hours. Similarly, if a certain second rate of wound irrigation (e.g., in terms of milliliters per hour) by sterile saline solution (and/or another liquid) is desired and the dressing cannot be changed more often than once every 24 hours, then the liquid supplying capacity of the dressing should be set to accommodate the second rate (desired irrigation rate) in combination with the expected duration of 24 or more hours between dressing changes.

Exudate absorption capacity and/or liquid supply capacity of a given dressing is generally a function of dressing thickness multiplied by dressing area. Manufacture and assembly of customized dressing layers tends to be time consuming and expensive. Accordingly, costs tend to go up and production rates down when custom dressings are requested with relatively large exudate absorption capacities and/or liquid supply capacities. An alternate option is disclosed here.

However, before examining the alternate option in more detail, it should be noted that a given patient may have multiple wounds (e.g., sores, ulcers, etc.) of different sizes, shapes, locations and morphologies. Depending on whether certain disease processes are present in different body regions and so forth, each wound site 120 may have a variety of differently characterized zones and each wound zone may have its own individual shape, topography, dimensions and treatment needs. As such, each wound site may have to be treated individually. By way of example, open wound site 120 of FIG. 1 is shown to have a centrally located, heavily exudating zone 140 at position $R_0$, and an overly dry, epitheliating wound zone 128 at first radial position $R_1$. In one embodiment, vapor concentration probes such as 104a, 104b may be used to approximately measure rates of exudate output and/or moisture loss (drying) in different zones of the wound 120 as is indicated in FIG. 1. The probed results may be transmitted to a digital data collecting device 104 which then forwards them to a coordinating computer that manages the design and fabrication of the custom dressing.

The illustrated wound site 120 is further shown to have a peri-wound zone 127 at second radial position $R_2$, and to have further away from the peri-wound zone 127, an adjacent and intact healthy skin zone 130 at third radial position $R_3$. A topmost skin layer 121 may cover the healthy adjacent skin 130 and may partially cover the peri-wound zone 127 and/or epitheliating wound zone 128. Peri-wound zone 127 may be inflamed or otherwise irregular due to the adjacent open wound 120. The illustrated wound site 120 is further shown to have a flexible tape ruler 103 placed near to it. (Not shown but contemplated here is that permanent ink marks are drawn on healthy skin adjacent to the ruler so that the ruler 103 can be removed and then later returned to substantially the same position and orientation.) In one embodiment, a color photograph (e.g., a digitized color image) is taken of the combination of the wound site 120 and adjacent ruler 103 so that dimensions and locations of various parts of the wound can be determined with reference to the adjacent ruler 103. In one embodiment, the adjacent ruler 103 extends to identifiable landmarks preexisting or added (e.g., marked) on the patient's body so as to thereby create a reproducible frame of reference and the taken image of the wound 120 and ruler 103 includes the identifiable landmarks.

Conventional wound dressings attempt to cover the entirety of the open wound site 120 and slightly beyond with a homogenous dressing material such as a woven 3 inch by 3 inch square of cotton gauze so as to at least prevent dirt and new bacteria (102b) from entering the open wound. By contrast and more recently, as mentioned above, it has been proposed to map and characterize a wound site such as 120 according to a variety of parameters including for example, by indicating which areas (zones) of the wound have too much liquid in them (too wet) and which have too little (are too dry) and which have a moisture concentration which is just about right and also the rates at which excessive drying is occurring or undesirable exudates are being discharged. Such characterizations of wound zones may be performed by a health care provider (e.g., doctor) with or without assistance from objective automated measurement tools (e.g., 104) that measure for example, local water concentration, vapor concentration, local pH, and so forth. Corresponding wound characterizing plots (not shown) may be generated to indicate relative degree of excess moisture and/or relative degree of excess dryness relative to respectively mapped X and/or Y frames of geographic reference (e.g., 103). Wound center region $R_0$ for example may be indicated to be too wet and the relative excess amount and rate of liquid production (exudate discharge rate) may be defined by quantitative information obtained form the care giver and/or assisting measurement equipment (e.g., 104). Epitheliating wound zone $R_1$ may be similarly indicated in this example to be too dry and the degree of excess drying as a moisture loss rate may be given by quantitative data points distributed over respective X and Y coordinate points.

One of the dressing design parameters that can be associated with a respective wound site mapping and characterizing plot is the rate (R, in milliliters per hour) at which liquid (moisture) should be removed from the underlying wound zone by one or more material layers of a corresponding, custom-designed wound dressing (see briefly, custom tailored dressing 209 of FIG. 2A). Such liquid removal profiles may be prescribed by a health care provider and/or automatically by a preprogrammed computer. In either case, if a given liquid removal rate (R) is to be maintained for a given number of hours, the corresponding customized dressing system should be designed to take up that amount of liquid and absorb and store the associated waste material (e.g., dried solids). Similarly, if a given liquid injection or irrigation rate (I) is to be maintained for a given number of hours, the corresponding customized dressing system should be designed to hold that amount of liquid and to be able to output it at the desired rate. A liquid removal/sourcing function plan for the given wound site 120 is often generated to indicate rates of moisture removal and moisture donation required from the dressing system and the projected durations over which those rates are to be maintained.

One of the ways in which moisture absorption rates can be controlled is by appropriate selective patterning of an out-gassing layer (see briefly 220 of FIG. 2A) in a multi-layered custom dressing. Details regarding how permeation from different areas of an out-gassing layer can be selectively controlled are provided in the above-cited U.S. Ser. No. 11/972,451 ("Wound Dressing with Controllable Permeability") whose disclosure is incorporated herein by reference. Briefly, microfiber pores (openings in a mesh of intersecting microfibers) may be closed or clogged in selected areas by thermal melting of polymer microfibers and/or by other means (e.g., addition of a clogging material) so that they no longer allow permeation of out-gassing vapors therefrom. Moisture absorption rates tend to follow up or down with vapor permeation rates. The faster that earlier absorbed moisture can have its water content out-gassed, the faster that new bulk moisture can be taken up from an exudating wound and vise versa. Outgassing rate tends to be a function of surface porosity and surface area. The larger the surface area is and the more porous it is (more vapor releasing openings), the faster it is that water vapor can be excreted through that surface.

Before delving further into these details regarding exudates absorption capacity, attention is first focused to FIG. 2A where a schematic diagram provides an overview of a custom-tailored product 200 that may be fabricated by automated machine means in accordance with the present disclosure. The custom fabricated product 200 includes a custom-tailored wound dressing 209 that is fabricated in accordance with the present disclosure to include, for example, custom tailored barriers 245 that are shaped and dimensioned to protect wound adjacent healthy skin when the dressing 209 is later applied to a corresponding wound (204c). More importantly for this disclosure, the custom dressing 209 includes one or more external access ports 225 which can interface with less customized expansion or extension parts. The custom wound dressing 209 is further custom patterned to provide different functionalities for different zones of an individual open wound site such as 120.

The product 200 includes a protective packaging 206/207/208 which is provided to sealing-wise house the dressing 209 and maintain the dressing in a clean or sterile environment prior to its application to a corresponding wound (e.g., 120). The protective packaging 206/207/208 also functions to route the contained dressing part 209 to the correct patient and corresponding wound. In one embodiment, the clean/sterile packaging 206/207/208 has a first sheet or layer 206 which is also referred to here as the base packaging sheet even though layer 206 is shown to be topmost relative to the +Z reference frame. Packaging 206/207/208 also has a second sheet or layer 208 (optionally thinner than layer 206) which is referred to here as the topside packaging sheet even though layer 208 is shown to be bottom-most relative to the illustrated +Z reference frame. Reasons for this will become clearer when the automated manufacturing process is described below (see briefly FIG. 3A). Packaging sheets 206 and 208 are flexible, gas impermeable and sealed together at their peripheries by applying appropriate pressure and/or temperature to a flexible, gas impermeable and pressure sensitive adhesive (PSA, pressure activated adhesive) ring 207 that is preformed on topside sheet 208. The PSA ring 207 is activated by for example applying an appropriate level of pressure to the outsides of the first and second packaging sheets 206 and 208 to thereby sealingly bond the first and second packaging sheets 206 and 208 to one another at their peripheries.

The base packaging sheet 206 may include an integral base labeling layer 205 that is provided as an integral part of sheet 206 where label layer 205 may for example be a thermally printable white surface onto which a thermal printer (not shown) can automatically print identification and other information as desired at the time that sheets 206/208 are sealed together by PSA seal 207 and dispensed with custom dressing 209 enclosed between sheets 206/208. The top side package sheet 208 may be composed of a transparent flexible plastic material which is gas impermeable as well as being impermeable to microbes or other contaminates. Packaging combination 206/207/208 is shown in FIG. 2 with its base sheet 206 on top (highest in the +Z direction) and its top side sheet 208 below because that shows the orientation of the enclosed dressing 209 as the latter is applied to a corresponding wound (e.g., 120). In other words, when dressing 209 is removed from the package and applied, an uppermost, liquid-permeable mesh layer 210 of the dressing is positioned on top to serve as an interface with the outside environment (102) and a liquid-permeable wound contacting layer (could be 250 or 240 or 230) is positioned below to interface with the wound and/or adjacent skin. During manufacture however, the base packaging sheet 206 is deposited first on a fabrication stage (see briefly 306-305 of FIG. 3A) and then the liquid-permeable mesh layer 210 as well as an integrally attached out-gas control layer 220 (liquid-impermeable) are deposited on the base packaging layer 206 as shall be detailed below.

Figure 3A:
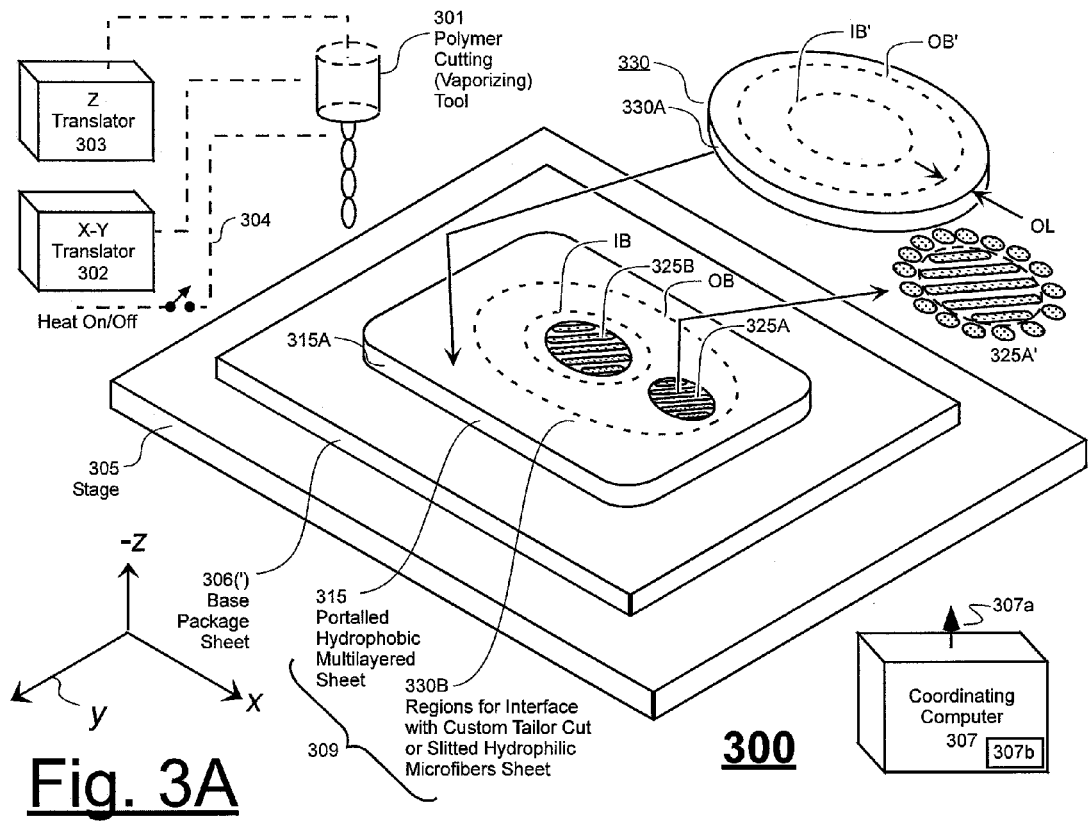
FIG. 3A is a perspective view of a first intermediate step in an automated fabrication process where a custom patterned dressing in accordance with the disclosure is being formed and where a hydrophobic multi-layered sheet section has been provided on a base packaging layer, and portal openings have been custom cut therethrough for providing paths for liquid communication with a first hydrophilic microfibers sheet section (also shown) of wound-matching dimensions that has been custom cut for deposition on the portalled hydrophobic sheet section.

Product 200 may optionally include a computer-printed adhesive identification label 204 attached to the exterior of the topside package sheet 208. In one embodiment, topside label 204 is automatically printed and thereafter attached to sheet 208 immediately after the package is sealed and dispensed for routing to a given wound on a given individual patient. The product 200 may thus have at least two patient identifying indicia formed thereon, one by means of topside label 204 and a second by means of base label 205. Optionally, a third label (not shown) with mailing information thereon and a backside adhesive covered by a peel off wax paper may be attached to label 204 by a perforated paper coupling. When product 200 is being inserted into a mailing envelope (not shown), the user tears off the third label (not shown) along the perforations and sticks it to the outside of the mailing envelope. Optionally, a fourth label (not shown) with mailing contents information printed thereon may be attached to label 204 by a perforated paper coupling. When product 200 is being inserted into a mailing envelope (not shown), the user checks off a check list on the fourth label (not shown) indicating which and how many dressing extension or expansion parts are being shipped together with the customized dressing 209. As will be seen shortly, the dressing extension or expansion parts may include porous foam pads that are designed to interface with the one or more external access ports 225 of customized dressing assembly 209. Optionally, further identifying indicia may be burned into or otherwise marked on an underneath side of layer 220 (or top of sheet 315 as the latter is shown in FIG. 3A). Although not shown in FIG. 2A, layers 210 and 220 generally extend out in the X and Y lateral directions substantially further than layer 230 so that layers 210 and 220 can be adhesively or otherwise secured to healthy skin. The underside of this extended part of layers 210/220 may have patient identifying and wound identifying indicia burnt thereon with a polymer burning tool or otherwise formed thereon (e.g., with color dyed silicone oil).

An example of patient/wound identifying and other functional indicia that may be provided is shown by way of example for the top side label 204 in the form of a magnifying glass symbol enlarged view 204. As seen, label 204 may include a first identification 204a of the specific patient for which the enclosed and custom tailored dressing part 209 has been fabricated and is intended to be routed to. The label may further provide routing information 204b indicating to whom next and how the sealed product 200 (along with an optional one or more separately packaged extension parts) is to be routed. For example it may indicate that the product 200 and optional extension parts are to be shipped directly to the patient's home or that they are to be routed indirectly to the patient by first hand delivering them to a pre-assigned caregiver (e.g., licensed nurse practitioner) who will then carry them to and assemble and apply them to the patient. It may further indicate the number of packaged extension parts that are to accompany the product 200 in shipment and it may identify those extension parts. The indicated method of routing may be by way of regular parcel post mail or by special delivery rush courier or by other means.

In one embodiment, the packaged and custom tailored dressing part 209 is not shipped or otherwise delivered simply by itself to the intended patient. Rather it is sent as part of a prespecified dressing assembly or composite system 290 (see briefly FIG. 2B) that has additional parts (e.g., non-custom or semi-custom dressing extension parts 260 and 270 of FIG. 2B) which will be assembled together just prior to or immediately after application of the custom tailored dressing part 209 to the intended wound site (e.g., 120). In that case, each of the non-custom or semi-custom dressing extension parts (e.g., 260 and 270 of FIG. 2B) may be packaged in its own respective and sterilely sealed package and each of those packages may have its own respective routing label like 204 that indicates which patient it is to go to, how it is to be routed there, and as will be explained shortly; which specific wound it is to be used for and how it is to be oriented on the patient. In an alternate embodiment, packaged extension parts have non-customized labels that merely indicate the type of extension part it is (e.g., liquid supplying like 260 of FIG. 2B or liquid absorbing like 270) and perhaps the liquid capacity of the extension part (e.g., expressed in milliliters) and perhaps an expiration date for use of the sterilely enclosed extension part. In an alternate or supplemental embodiment, packaged liquid supplying extension parts like 260 of FIG. 2B may be packaged with prespecified liquids (e.g., saline, antibiotic, etc.) and/or prespecified solids predeposited inside their porous interiors, in which case the packaging label will also indicate what liquids and/or solids are included. Liquid absorbing extension parts like 270 of FIG. 2B may be packaged with their porous interiors being dry or pre-infused with antimicrobial so as to prevent colonization of the extension part by microbes and leach back of the microbes into the wound, in which case the packaging label will also indicate what antimicrobials, if any, are included. In an alternate or supplemental embodiment, packaged extension parts like 260 and 270 may be fully customized through fabrication, for example, in an automated assembly line that custom cuts foam or other parts to specified size, infuses the foam with custom specified addends, deposits the appropriate outer skin around each customized foam part, forms the extension part portal(s), and then packages the extension part. In such a case the package labeling for the packaged extension parts may be just as complex as that used for the primary custom wound dressing 209.

The top side label 204 of illustrated package 206/207/208 of FIG. 2B may identify the specific wound site (e.g. 120) for which this specific custom dressing part 209 has been designed. Wound location identification may include one or more graphic images 204c such as schematic diagrams of a human body front and back with a spot marker indicating exactly where the primary wound dressing part 209 is to be placed on the given patient 204a and in what orientation. In the case where dressing extension parts like 260 and 270 of FIG. 2B are present, the wound location identification indicia 204c may further show how the extension parts (e.g., 260, 270) are to be oriented relative to the primary wound dressing part 209 and/or relative to the patient's body (e.g., wrapped spirally around a leg for example). Wound location identification may further be provided by color coding of the topside label. For example, a patient or care giver may be taught that a label 204 that is half green-colored and half orange colored means this dressing goes on the right leg and it is to be supplemented with one green-colored extension part (e.g., 260) and one orange-colored extension part (e.g., 270). On the other hand, another label 204 that is all yellow might mean the enclosed primary dressing goes on the left leg and there are no extension parts to go with it.

Label 204 may further provide date/time indications 204d that indicate dates (and/or specific times) on which the custom dressing 209 (with or without corresponding extension parts) is to be applied to the wound and thereafter respectively removed. In some instances, a plurality of sealed custom products like 200 and optionally a plurality of sealed semi-custom or non-custom products like 260, 270 (whose packages are not shown) are custom compiled as a kit at a same time under coordination of a care coordinating computer program (see briefly 507b of FIG. 5B). The compiled but individuality sealed custom, semi-custom and/or non-custom parts are sent in unison to the patient or nurse for respective assembly and/or sequential application to the patient over a doctor prescribed sequence of dates and/or times. In such a case, each primary dressing part (e.g., 209) may have its own one of sequential and unique identification numbers (e.g., Rx numbers, not shown) included on label 204. Information 204d indicates the doctor-prescribed application and removal dates/times for its contained dressing.

The attached label 204 may further include more detailed instructions 204e for application and/or removal of the correspondingly enclosed dressing part 209 including for optional attachment of one or more extension parts like 260, 270 where appropriate. For example, the prescribed application of the custom tailored dressing 209 may call for provision of medicines or ointments to the wound or to the primary dressing 209 or to the extension parts (260, 270) prior to assembling and applying the combined dressing (e.g., 290 of FIG. 2B) to the wound site. Alternatively or additionally, the prescription may call for addition of such medicines, ointments, oils, etc. to the dressing 209 or its extension parts (260, 270) after assembly and application to the wound site. In one embodiment, an address of an internet web page (e.g., www.private123.com) is given on the label 204 and when opened with use of a computer, the identified web page (e.g., a password secured page) provides detailed instructions for dressing assembly, application and removal as well as a repeat of the patient identification information 204a and wound identification information 204c provided by label 204. Thus the whole of packaged product 200 is seen to be the whole of or part of a functional combination or dressing system (290) that is operatively routed to the intended patient (101) and intended wound (120) for application thereto in a prescribed orientation at the doctor prescribed date and time 204d and with optional addition of doctor prescribed addends (e.g., extension parts 260, 270 and/or further medicines, moisturizers, etc. as specified by instructions 204e). Each part of the combination is routed and delivered to the patient in sterile or clean form thanks to the enclosing package and associated labeling (e.g., 204). In one embodiment, the custom wound dressing 209 and enclosing packaging 206/207/208 as well as associated routing and/or use information (204a-c, 204e) and optional labels for semi-custom or non-custom extension parts (260, 270) are automatically produced under control of a single coordinating computer program (e.g., 307b executing for example in a single coordinating computer—see 307 of FIG. 3A, or across a networked computing cloud) so as to assure that the correct primary dressing (209) and optional extension parts (260,270) will be routed to the correct patient and applied to the correct wound at the right time with correct associated usage instructions. This helps to reduce the possibilities for foul up in each of the various steps that span from wound assessment and treatment formulation to treatment delivery. A user-friendly combination 200/290 is thus automatically manufactured and provided with associated informational indicia integrated thereon for assisting in routing the enclosed dressing parts 209, 260, 270 to the intended patient 204a and to the intended wound 204c and for application of the dressing parts on the wound as intended by the prescribing care provider (e.g., doctor).

Referring to the topmost dressing layer 210 in FIG. 2A, and to the magnification 201 thereof, this topmost layer 210 may be fabricated as a porous sheet material composed of a non-woven mesh of stuck together polymer microfibers where the microfibers are hydrophobic in nature, nonsoluble in water and provide a strong outer and scuff-resistant interface for interfacing with the external environment (102 of FIG. 1A). Average and/or median pore size between the intersecting microfibers of interface layer 210 is sufficiently large to easily let bulk water droplets through and as well as gases (e.g., water vapor) through. Any of a variety of relatively strong polymers may be used for forming microfibers layer 210, preferably those with low friction and good scuff resistant properties. Methods for forming microfiber meshes are disclosed for example in the above-cited U.S. Pat. No. 7,105,058 whose disclosure is incorporated herein by reference. The present disclosure is not limited to the methods described in U.S. Pat. No. 7,105,058.

The second layer 220 of dressing 209 is also composed of a porous sheet material such as one composed of a non-woven mesh of hydrophobic intersecting polymer microfibers. However the average and/or median pore size between the microfibers of layer 220 (see magnification 202) is extremely small; generally less than about 0.5 micron and better yet, less than about 0.2 micron. As such, the pores are sufficiently small to block microbes and bulk water droplets from passing through. However these micro pores are sufficiently large to let one or more desired gases through such as water vapor. Thus, the second layer 220 forms a liquid impermeable and microbe impermeable barrier layer or filter that can block infected solid particles in exudates (e.g., 141 of FIG. 1A) from rising out of the wound 120 in the +Z direction and thereafter continuing to ooze out through the topside of the dressing 209. The second layer 220 also prevents contaminated bulk liquid droplets or particles (e.g., 102b of FIG. 1A) from entering into the dressing in the −Z direction. However, water vapor and/or other gases may permeate into or out of the dressing by way of the second layer 220. Different regions of layer 220, such as 222 may be custom patterned (e.g., selectively clogged) to further limit or to totally block out-gas permeation through those custom adjusted zones (222). Examples of how such custom control may be realized are disclosed in the above-cited U.S. Ser. No. 11/972,452 ("Wound Dressing with Controllable Permeability") whose disclosure is incorporated herein by reference. The disclosed methods include selective heat melting of a bottom portion (as shown by area 222 in FIG. 2) of layer 220 with hot sterile air or with laser beams or other such selective heating means so as to melt the fibers in those selected zones and thus create a non-permeable film areas thereat. In one embodiment, second layer 220 is provided as an integrally fused part of a multilayer sheet material that also includes top layer 210. The fused multilayer sheet material 210/220 is stretched over a fabrication stage (see briefly 305 of FIG. 3A) and a custom shaped portion thereof is cut out with a cutting tool (301) and dropped onto the stage under directions of a fabrication coordinating computer 307. In one embodiment, the first and/or second layers 221/220 have one or more through holes such as 225 formed therethrough (or perforations whereby cylindrical section 225 can be torn out) so as to allow coupling of liquids through the through holes 225 to or from an external liquid storage means. The through holes or tear-out perforated sections 225 may be pre-sealed with an impermeable polymer film or with a peel-off wax paper or the like that can be selectively removed with a corresponding solvent during automated dressing fabrication. This is done under direction of a fabrication coordinating computer 307 when the through hole or port section 225 is intended to be opened up for operative coupling to an external liquid storage means (e.g., a solid foam pad that is presoaked with and stores a prespecified volume of sterile normal saline solution for subsequent release into the wound via the custom wound dressing part 209).

Moreover and importantly for this disclosure, cutouts, through slits and/or through holes or perforations may be formed as standard or custom tailored features through the combination of layers 210 and 220 to define liquid input and/or output ports such as 225 through which liquids may be moved between the exterior of dressing 209 and a next-described layer 230 when such movement is desirable. The liquid transfer port 225 will be described in more detail below.

Still referring to FIG. 2A, a third layer 230 of the custom dressing 209 is composed of a porous material such as one composed of hydrophilic microfibers where in some embodiments these may also be thermally meltable microfibers. Magnification 203 shows that the pores between the intersecting polymer microfibers of layer 230 are of medium size so as to let through both bulk liquid droplets and gases. The general use of this third layer 230 is to either absorb liquids into itself (into its pores and/or onto its internal surface areas) and/or to store and donate clean moisturizing liquids to the wound depending on corresponding wound region and treatment needs of the corresponding wound region. The to-be-absorbed liquids may include exudates 141 emerging from the underlying wound As shall be detailed shortly, flow control barriers 243 such as those for controlling flow of aqueous solutions may be selectively formed as custom patterns that extend either entirely through the thickness of this third layer 230 or extend partially through the thickness of layer 230 as desired and in desired locations thereof. In one embodiment, barriers 243 subdivide third layer 230 into a central zone (corresponding to $R_0$ of FIG. 1A) that is kept dry during fabrication and a peripheral (but not to the edge) zone that is filled with sterile saline solution during fabrication. Upon application of the custom dressing 209 to a corresponding pre-mapped and pre-characterized wound such as 120 (FIG. 1A), the pre-moisturized peripheral zone aligns with and donates moisture to a first wound zone that had been pre-characterized as a too dry wound periphery (e.g., 125). The non-moisturized central dressing region aligns with and absorbs exudates from a second wound zone that had been pre-characterized as being excessively wet. Thus each wound zone is specially treated according to its needs by a corresponding dressing region.

In some embodiments, the packaged custom dressing 209 is composed of just the first three illustrated layers 210, 220, and 230 which are fastened to one another. In other embodiments additional layers may be included such as the illustrated fourth layer 240. In one embodiment, layer 240 is composed of hydrophilic microfibers with capillary soak-up capabilities for drawing liquids up or down through layer 240. Layer 240 has a corresponding bottom major surface 241 and layer 230 has a corresponding bottom major surface 231. When a given liquid is transported into or out of the bottom of layer 240, the bottom area for flow of that liquid through bottom surface 241 is not necessarily the same as the surface area used for moving that same liquid (e.g., exudate) through an area in the bottom surface 231 of layer 230. Funneling barriers or other liquid flow controlling barriers such as 243 may be fashioned so as to define different surface areas for liquid inflow or liquid outflow at respective bottom surfaces 241 and 231 of respective layers 240 and 230. Additionally or alternatively, partial flow barriers such as 245 may block parts of lower surface 241 from passing liquids therethrough as will be detailed below. In either case, by adjusting the amount of surface area 241 available for transport of different liquids through the bottom of layer 240 and by adjusting the liquid pass-through surface areas at interface 231, a designer of custom dressing 209 (which designer can use a computer to assist in the design) may alter the rates at which different liquids move from one layer to the next and/or may alter the amounts of liquids absorbed or donated from one layer to the next and/or to/from corresponding wound zones. Thus the ability to create custom barriers like 243 and 245 in the custom wound dressing part 209 gives the dressing designer an ability to better custom tailor the functions provided by the dressing 209 to match the treatment needs of a corresponding individual wound 120 and its pre-mapped and pre-characterized wound zones.

The fifth, wound-interfacing layer 250 is also optional. It is shown for the purpose of demonstrating that different areas of the dressing that interface with the actual wound may have different local interface chemistries 252 depending on which chemicals are custom tailor wise donated into region 252 or removed from interface region 252 and also depending on the differing rates at which these various chemicals are transported out of or into the respective dressing regions.

The actual wound itself which alignably underlies interface surface 251 is of course not present inside packaging 206/207/208 but it is nonetheless shown in phantom in FIG. 2A in order to show how a first pre-characterized wound zone 291 that is deemed to be too wet and thus requiring absorption of exudates therefrom aligns with a funnel connected, and enlarged, absorbing volume in layer 230 and with a high gas permeation area of layer 220. It also shows how a second pre-characterized wound zone 292 that is pre-characterized to be too dry and thus requiring of the dressing to donate moisture to that area 292 is aligned with a barrier bounded, liquid donating volume of layer 230 (bounded by custom formed barrier 245) and overlaid by a blocked gas permeation area 222 of permeation control layer 220.

With the overview of labeled and packaged product 200 now in place, attention is directed to a specific automated manufacturing process. FIG. 3A is a perspective view showing a custom tailored dressing 309 at an intermediate state during its automated manufacture. The automated manufacturing process 300 includes the provision of a supporting stage 305 such a rigid flat metal plate. A base sheet 306 of a to-be-formed sealing package is stretched out over the stage, flattened thereon by for example moving a combination of supply and take up reels towards the supporting stage 305 or vise versa. Each step in the automated manufacturing process 300 may be controlled by a fabrication and packaging coordination program executing for example on a local process coordinating computer 307. Computer 307 is understood to have appropriate hardware and software components including one or more data processors, memory, network interface, and I/O interface circuitry (represented by 307a) for interfacing with and controlling the various computer controlled mechanisms described herein including a motorized means (not shown) for dispensing base packaging sheet 306 onto the support stage 305 and then moving the base packaging sheet 306 off beyond the support stage 305 for dispensing after the base sheet 306 is sealed together with a top packaging sheet (not shown).

After sheet 306 is deposited, in a next step of the automated process 300, a multi-layered hydrophobic polymer microfibers sheet (not fully shown) is dispensed in stretched form above and vertically spaced apart from the base package sheet 306. Such dispensing of the multi-layered hydrophobic polymer microfibers sheet is performed by a corresponding sheet dispenser (not shown) under control of computer 307. A pre-specified outer peripheral shape 315A (e.g., rectangle with rounded corners) of prespecified dimensions is cut out from the dispensed and overlying hydrophobic multi-layered sheet (not shown) under control of computer 307, and then deposited (e.g., dropped) on a prespecified region of the base package sheet 306 and flattened thereto. Multi-layered sheet section 315 (having outer shape 315A) corresponds to layers 210 and 220 of FIG. 2A. In one embodiment, a high temperature polymer cutting tool (polymer vaporizing tool) 301 is used to cut out the shape 315A of shaped sheet section 315 from a larger dispensed and stretched sheet (not shown). In one embodiment, the polymer cutting tool 301 includes a ceramic cylinder that supports a twisted nichrome wire emerging from a bottom portion thereof. The nichrome wire (e.g. having FIG. 8 twisting) and its holding ceramic tube are operatively coupled to and translated by an X-Y position translator 302 that is controlled by coordinating computer 307. The cutting tool 301 is further connected to and translated by a computer-driven Z translator 303. Moreover, a computer-driven electric switch 304 selectively couples electrical power to the nichrome wire so as to turn its heating on and off for providing a desired temperature, where a fully on state produces a polymer vaporizing temperature that vaporizes the material surrounding sheet section 315. In operation, the cutting tool 301 is first positioned by the X-Y translator 302 above a start point of a computer-defined cutting path. The heat is turned on (by actuating switch 304) and then the Z translator 303 lowers the tool 301 to thus create a vaporized hole at the point of decent and optionally to begin a polymer vaporizing traverse along a predefined X-Y cutting path (e.g., 315A). When the positioned through hole and/or predefined cutting path is finished, the Z translator lifts the tool 301 up and the heating switch 304 is turned off. The outer shape and dimension 315A of the hydrophobic multilayer sheet section 315 is thus defined to correspond to a pre-mapped and pre-characterized wound or wound zone. During the cutting, positive air pressure is maintained in the process chamber (not shown) that houses stage 305 and tool 301 so that the vaporized polymer material created by tool 301 escapes to a lower pressured ambient atmosphere via minute openings in the housing.

In one embodiment, before the outer periphery shape 315A of hydrophobic sheet section 315 is cut and dropped onto the stage 305 and the base package sheet 306, and while the material from which sheet section 315 will be cut is stretched over the stage 305, one or more standard or custom portal holes such as 325A and 325B are cut through the area that will form the shaped hydrophobic sheet section 315. The portal holes (e.g., 325A, 325B) may take on any of a variety of shapes, sizes and locations as determined by the fabrication coordinating computer 307. In one embodiment, first portal hole(s) 325B are defined inside a pre-defined inner boundary (IB) and second portal hole(s) 325A are defined inside a pre-defined outer boundary (OB) but not crossing over the pre-defined inner boundary (IB). As will be seen in FIG. 4A, the inner boundary (IB) and outer boundary (OB) respectively correspond to inner and outer water repelling barriers 443, 445 that will be formed in a next deposited hydrophilic sheet section 330. In one embodiment, one or both of the first and second portal hole(s) 325A and 325B are defined to include parallel linear slits cut by vaporizing tool 301. An example of such parallel slits (linearity is optional) is shown in magnified view 325A'. In one embodiment, one or both of portal hole(s) 325A and 325B are defined to include perforations holes defining their outer extremes. Alternatively or additionally, one or more of the through holes may function as a liquid transfer hole rather than as a perforation hole. An example of such perforation and/or liquid-transfer holes is shown in magnified view 325A'. A user may be instructed (e.g., by instructions 204e of FIG. 2A) to tear out the material inside of pre-formed perforation holes and thus create a larger portal hole area. The parallel through-slits need not be present in the latter case.

In one embodiment, before the outer periphery shape 315A of hydrophobic sheet section 315 is cut and dropped onto the base package sheet 306 and stage 305, and while the sheet material of sheet section 315 is stretched above and over the stage 305, cutting tool is used to cut large portal holes through the area of section 315 such as ones encompassing the full areas of illustrated portal holes 325A and 325B. In this variation, the cut-out excess material of sheet section 315 is dropped onto base sheet 306, where the latter is now referred to as a first sacrificial base packaging sheet 306. Then, before outer shape 315A is cut and the full sheet section 315 is dropped down toward stage 305, the first sacrificial base sheet 306 is advanced (moved) off beyond stage 305 and a new, second base sheet 306' is advanced (e.g., by rollers, not shown) onto stage 305 to take the place of first base sheet 306. The debris or excess sheet material generated by the cutting of the relatively large portal holes is thus carried away from the stage by the advancement of the first base sheet 306 off the dressing assembly stage 305. Thereafter, the outer peripheral shape 315A of section 315 is fully cut and dropped down onto the second base sheet 306'. The first base sheet 306 may be discarded with the cut out sheet material of the portal holes as production waste. An also-to-be-discarded top package sheet (not shown) may be further adhered to the first sacrificial base sheet 306 as the two are ejected from the dressing fabrication chamber for discard.

Using one or more of the above described portal hole(s) defining methods or variations thereof, one or more liquid transfer portals (e.g., 325A, 325B) may be defined through the hydrophobic multilayered sheet section 315 where the defined liquid transfer portals have pre-specified locations, pre-specified dimensions, pre-specified shapes and/or pre-specified cross sectional areas for allowing liquid flow therethrough as defined or determined under control of the fabrication coordinating computer 307. The liquid transfer portals (e.g., 325A, 325B) will cooperate with later added dressing extension parts such as 260 and 270 of FIG. 2B.

Still referring to FIG. 3A, in a next computer controlled step the out-gassing permeation rates of different areas of the cut out sheet section 315 (except for areas thereof forming external portal holes such as 325A, 325B) are optionally varied in accordance with the above-cited U.S. Ser. No. 11/972,451 whose disclosure is incorporated herein by reference. In one embodiment, a computer controlled hot air blower (see 408 of FIG. 4A) is used to selectively melt polymer fibers in select subsections of cut out sheet section 315. The hot air melt technique may be optionally used to change (e.g., shrink) the dimensions of external portal holes or slits such as those shown in magnification 325A'.

Next, a second porous material sheet such as one composed of hydrophilic microfibers is stretched over the precut hydrophobic sheet section 315 by action of a corresponding second sheet dispenser. This second porous material sheet is pattern cut to have outer peripheral shape and dimensions 330A under control of the coordinating computer 307 and again with use of tool 301. The cut out section 330 of the second dispensed porous sheet (shown spaced apart from sheet 315 so that portals 325A, 325B can be seen) is thereafter dropped onto to the stacked combination of base package sheet 306(') and the cut out hydrophobic multilayered sheet section 315. Cut out section 330 is fastened to earlier cutout section 315 by spot heat welding or otherwise. In one embodiment, the automatically shaped, dimensioned and deposited hydrophilic microfibers sheet section 330 corresponds to layer 230 of FIG. 2A. Although in one embodiment, sheet section 330 is provided as a single layer of hydrophilic porous material, it is within the contemplation of the disclosure to instead provide sheet section 330 as a combination of multiple layers of differently behaving hydrophilic porous materials that have been prefused together or otherwise joined to one another. For example, such a combination of different hydrophilic porous material layers may be composed of successive layers with successively reduced or successively increased average or median pore sizes and/or with successively reduced or successively increased degrees of hydrophilicities.

As part of the design for the custom tailored cutting of the hydrophilic porous sheet section 330, a certain overlay region (OL) may be pre-specified where the custom-shaped sheet section 330 will overlay on healthy or peri-wound skin. The shape and dimensions of the pre-specified overlay region (OL) may be stored in an operational memory of computer 307 along with specifications for inner and outer boundaries IB' and OB' shown in phantom on sheet section 330. The inner and outer boundaries IB' and OB' correspond to respective inner and outer boundaries IB and OB shown in phantom on lower sheet section 315.

Figure 3B:
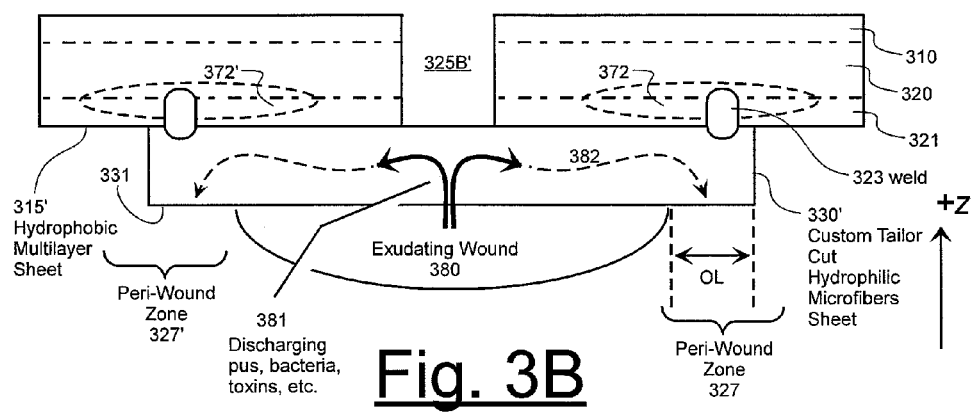
FIG. 3B is a side sectional view showing how the wound-matching hydrophilic microfibers sheet section of FIG. 3A is intended to overlay peri-wound and/or healthy skin adjacent the open wound and how exudates may flow out through one of the custom located portals.

Referring to FIG. 3B, a side sectional view is provided showing how the wound-matching hydrophilic porous sheet section 330 of FIG. 3A is intended to align with overlay peri-would zone 327 when the custom dressing 309 is later aligned over and applied to its corresponding wound 380. Portal hole 325A is not shown in FIG. 3B so as to avoid illustrative clutter. As seen, portal hole 325B aligns over a region hydrophilic sheet section 330' so that some of the exudates and/or water vapor taken up from the wound 380 by hydrophilic sheet section 330' can transfer through portal hole 325B for further absorption by a dressing extension part such as 270 of FIG. 2B. Additional details of FIG. 3B are that the hydrophobic multilayer sheet section 315 may include a wide-pores layer 310, an ultra narrow-pores layer 320 and a spot weld-forming lowest layer 321. The melting temperature of fibers in lowest layer 321 is lower than the melting temperature of fibers at the bottom of layer 320 or the top of layer 330. Thus, when a computer-controlled spot welding tool (not shown) having a temperature lower than the melt temperatures of layers 330 and 320 but higher than the melt temperature of layer 321 is compressively applied at a pre-selected weld point 323, fibers in layer 321 melt and infiltrate into layer 320 above and layer 330' below to thus form a spot weld of molten material extending between and into layers 320 and 330. When the welding tool is removed, the weld 323 solidifies and thus securely attaches sheet 330 to layer 320. Prior to formation of the weld 323 however, different areas 372 of layer 321 other than where the spot weld 323 will be formed may optionally be pre-melted to flow into layer 320 so as to clog gas permeating pores in layer 320 and thus custom adjust gas permeation rates through layer 320. These selectively pre-melted areas are represented by ellipses 372 and 372'.

Still referring to FIG. 3B, a problem can emerge when a multilayered dressing structure such as that shown in FIG. 3B is applied to a heavily exudating wound 380. The liquids 381 which rise up out of the wound 380 and into the lowest layer 330' (e.g., hydrophilic layer) may include undesirable components such as pus, bacteria, and toxic chemicals, bacteria, etc. generated within the wound and removed therefrom as part of absorbed upflow 381. Because layer 330', in its still unpatterned form (no liquid barriers yet formed), is isotropically hydrophilic, the absorbed exudates 381 can continue to diffuse laterally (in the X and Y directions) along phantom path 382 and thus migrate to the overlay area (OL) where dressing material 330' directly overlays on the peri-wound zone 327 and/or on adjacent healthy skin. These laterally migrating exudates 382 may damage or degrade the overlaid peri-wound zone 327 or adjacent healthy skin area (not shown) and thus undesirably cause an expansion of the wound as opposed to promoting healing. The inner diameter of the overlay area (OL) is defined in FIG. 3A by the dashed outer boundary (OB'). In one embodiment, such lateral exudates movement is blocked by erecting custom tailored liquid flow barriers as will now be explained.

Figure 4A:
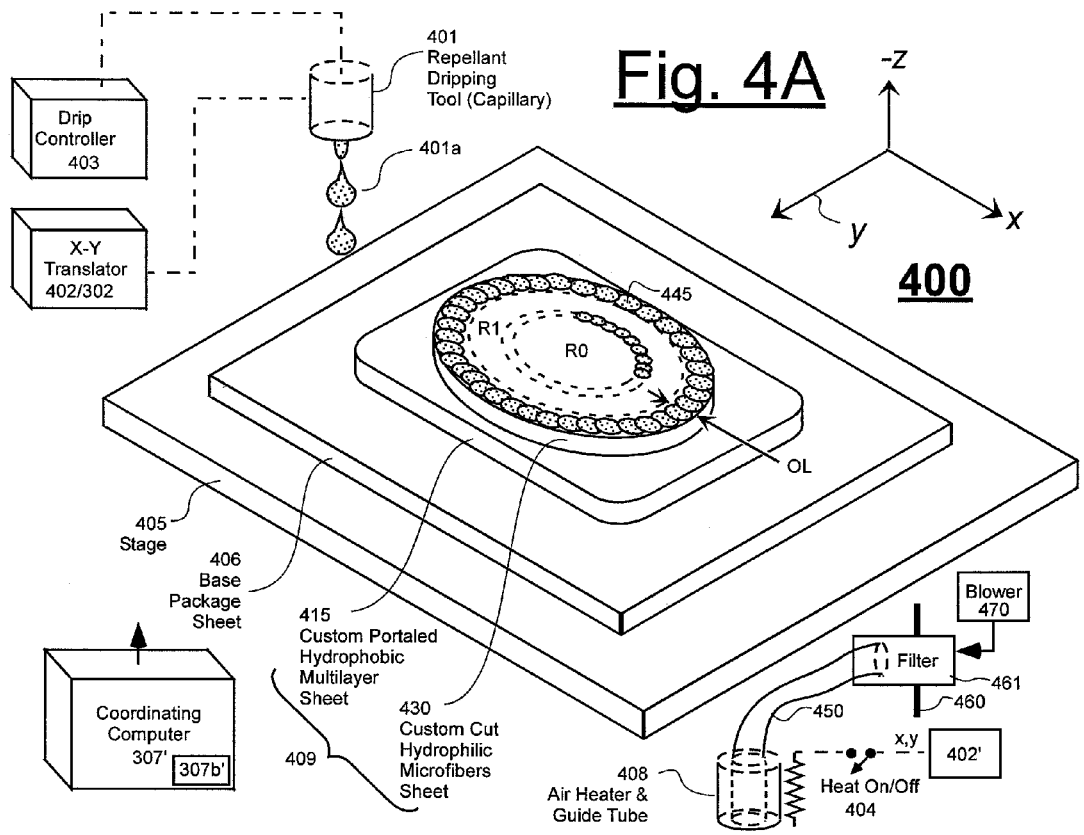
FIG. 4A is a perspective view of a second step in an automated fabrication process where a custom patterned dressing part in accordance with the disclosure is being formed and fluid blocking barriers of predefined dimensions and shapes are being formed in the first hydrophilic microfibers layer.

Referring to FIG. 4A shown is a perspective view of a next step 400 in the automated process 300-400 for fabricating the custom-patterned dressing under control of a coordinating computer program 307b executing in computer 307' and/or elsewhere. The further refined dressing is now denoted as 409 and hydrophilic sheet section 430 (corresponding to 330 of FIG. 3A) is now shown as deposited on and spot welded or otherwise fastened to hydrophobic layer 415. In accordance with one aspect of the present disclosure, a first liquid flow blocking barrier 445 is now custom formed within the overlay region (OL) of the hydrophilic sheet section 430 (in other words, peripherally exterior of outer boundary OB' of FIG. 3A) so as to thereby block laterally diffusing and potentially harmful liquids such as exudates 482 (or moisturizing saline solution loaded into dressing region R1) from reaching and possibly degrading the overlaid skin or peri-wound areas (OL). This liquid blocking barrier material 445 is preferably formed from a material 401*a* which is itself non-toxic and not damaging to the overlaid skin zone 327 that is will lie over. Examples of flow blocking materials that may be used include water repelling materials (hydrophobic materials) such as silicones, silicone oils, mineral oils and vegetable oils. One or more of these skin-safe but water flow blocking materials may be purchased or custom formulated (e.g., by appropriate distillation) to provide desirable viscosity, surface tension, capillary attraction and/or other properties as is detailed in the above-cited and here incorporated U.S. Ser. No. 12/164,451 filed Jun. 30, 2008.

The chosen or custom formulated water repellant substance or substances is/are picked to have sufficiently moderate viscosities so that they can infiltrate relatively quickly into the porous microstructure (e.g., microfiberous matrix) of the liquid transport or liquid storage layer 430 in which it/they are to be embedded, generally in a substantially fixed manner. The combined characteristics of layer 430 and the utilized water repellant substance(s) 401*a* are such that after liquid 401*a* infiltrates in the +Z direction into a desired area of the target layer 430 (e.g., the wound-interfacing layer 430) to a desired depth, liquid 401*a* becomes resistant to further migration and it substantially maintains its post-infiltration shape and location in the porous microstructure when under normal (e.g., room or body) temperature and/or other normal operating conditions. In other words, after having been deposited in the +Z direction onto the upward facing surface 431 of cutout sheet 430 of the FIG. 4A during the automated manufacturing process 400, the infiltrating blocking material 445 holds itself together within the microstructure of the infiltrated porous layer 430 under normal dressing-use conditions due to one or more of viscosity effects, surface tension effects, microfiber capillary drawing effects and/or other effects so as to substantially maintain an outline of its deposited and embedded pattern and to thus function as a barrier against the flow of aqueous fluids (e.g., exudates) therethrough. In one embodiment, a silicone with a viscosity in the range of 1 centiStoke to 1000 cSt is used with a nominal value of around 5000 cSt. In another embodiment the viscosity of the utilized silicone is in the range of 100-1000 cSt with a nominal value of about 500 cSt. The specific viscosity used will vary from case to case depending on the porosity and/or other characteristics of the wound interfacing layer 430. In one embodiment, medications or vitamins (e.g., vitamin E) are mixed in with the utilized silicone or other water repelling liquid 401*a* so as to promote skin health at the region where the skin overlying outer barrier 445 is formed to contact with a corresponding skin area.

In one embodiment, a viscosity-lowering solvent is mixed together with an otherwise high viscosity, water repelling material. The mixture 401*a* of solvent(s) and water repelling material(s) is then selectively deposited as drops over the overlay region (OL), for example by using a repellent mixture dripping tool 401 whose position and drip rate are controlled by coordinating computer 307'. As seen in FIG. 4A, dripping tool 401 (e.g., a flexible tube) of one embodiment is operatively coupled to and translated by the same computer-driven X-Y translator 402/302 as used for controllably translating cutting tool 301 of FIG. 3A. The repellent dripping tool 401 is also operatively coupled to a computer-controlled drip rate controller 403. Droplets 401*a* are released at an appropriate rate corresponding to movement by the X-Y translator 402 after the translator has brought the dripping tool (capillary) over a desired start point where the to-be-embedded barrier 445 is to be formed. After the water repellent material 401*a* with its included viscosity-lowering solvent infiltrate into the wound-interfacing layer 430 at normal room temperature, the material is heated to an above-normal temperature but not one at or above the melt temperature of the dressing polymers. The raised temperature volatilizes and removes the viscosity-lowering solvent and/or at the same time temporarily reduces the viscosity of the left behind barrier material so that the latter may diffuse vertically and/or laterally by a predetermined amount. Localized heating may be provided for example with an X-Y driven hot air guiding tube 408 such as shown in FIG. 4A. After the solvent is driven off and temperature of the left behind water-repelling material 445 returns to room temperature, the viscosity of this left behind water-repelling material 445 is substantially reduced and its self coherence is increased due to removal of the solvent and stoppage of localized heating. As a consequence, material 445 retains its post-deposition and post-infiltration shape and thickness as well as its relative position within the dressing material. By overlapping deposited drops 401*a*, a continuous barrier 445 may be formed that fully covers the to-be-protected surrounding skin of a given wound. Of course, the protective barrier may alternatively be patterned to be other than fully continuous and fully covering (e.g., it may be patterned as a plurality of spaced apart dots). The specific pattern created under control of fabrication coordinating computer 307 may vary and depend on the specific treatment plans devised for the corresponding wound dressing 409 by a prescribing health care provider.

In one embodiment, heating tool 408 receives filtered air (e.g., microbe free air) through a flexible plastic tube 450. The air heating tube and an included resister (heating element) thereof are translated by X-Y translator 402/403. Electric heating of the resistive element in tube 408 is controlled by a computer-driven on/off switch 404. Filter 461 protrudes through a relatively air-tight chamber casing 460 where the later houses the in-fabrication dressing 409. The air filter 461 has pore sizes sufficiently small to block out microbes from entering into the sterile interior environment of the casing 460. Blower 470 maintains positive air pressure within the casing interior so that unclean air cannot enter. Prior to use, the barrier forming material 401*a* is kept in essentially sterile condition so that its introduction into layer 430 will not inadvertently contaminate the dressing with harmful microbes. In one embodiment, prior to use in fabricating dressings, one or more of the barrier forming material 401*a*, the drip tool 401 and the heating tool 408 (as well as flexible tube 450 and filter 461) are subject to gamma irradiation of sufficient intensity to render them medically sterile.

Figure 4B:
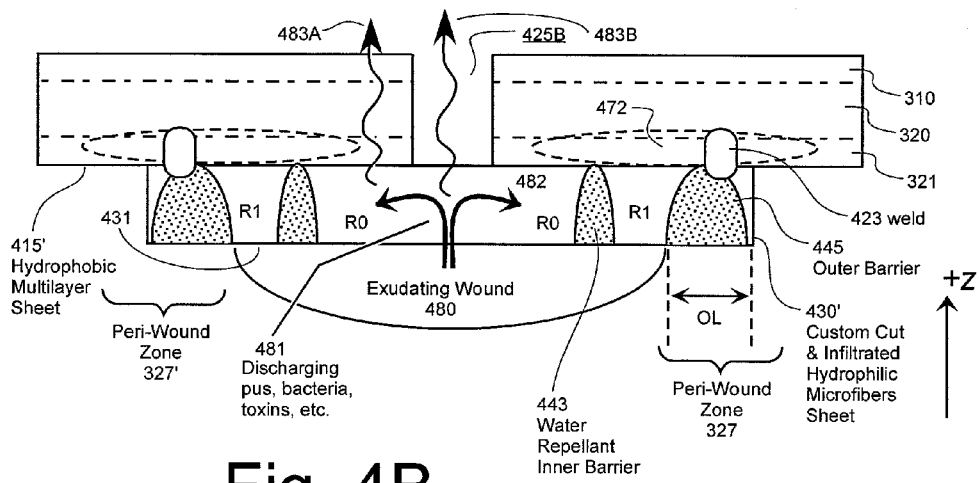
FIG. 4B is a side sectional view showing how the wound-matching fluid blocking barriers of FIG. 4A are intended to align with and overlay respective exudating, dry and peri-wound and/or healthy skin regions adjacent the pre-measured and pre-mapped open wound and how one liquid funneling region aligns with a corresponding portal.

In addition to forming the outer protective barrier 445 for blocking harmful fluids from laterally crossing outer boundary OB and reaching the skin overlay region OL, additional custom shaped and dimensioned water repellent barriers such as 443 may be formed through the thickness of the wound-interfacing layer 430' as shown in FIG. 4B where the position of formation corresponds to inner boundary (IB, IB') of FIG. 3A. In the illustrated example, dressing region R1 corresponds to epitheliating wound zone 128 of FIG. 1A. Since in the given example it is desirable to keep the epitheliating wound zone 128 somewhat moisturized while preventing the exudating discharge 381 from the center of the wound 140 from reaching epitheliating wound zone 128; the inner barrier 443 is custom patterned to fully surround exudating wound zone R0. Additionally, after the inner barrier 443 is embedded into layer 430', a moisture providing liquid such as clean water or saline solution or a medicine containing solution is deposited into the barrier embraced, intermediate region R1 of layer 430'. (Additional volumes of water, saline solution and/or medicine containing solutions may be provided in one or more dressing extension parts like 260 of FIG. 2B and transferred through portal holes like 225A as will be explained shortly.) Outer barrier 445 keeps the introduced moisturizer from reaching the overlaid skin of overlay zone OL. Inner barrier 443 keeps the introduced moisturizer from being contaminated by exudates that enter central region R0 of layer 430'. The gas impermeable patterned region 472 overlying and engaging with barriers 443 and 445 keeps the deposited moisturizer of dressing region R0 from evaporating away into the ambient. Accordingly, the prescribed moisturizer in dressing region R0 is directed to only the pre-mapped wound zone where it is intended to be applied and it is blocked from dissipating wastefully or harmfully into other areas. It is to be noted here that even in the case where the prescribed moisturizer in dressing region R0 is simply clean water, the latter can damage or degrade adjacent skin if the skin is exposed to the water for too long of a time. However, the silicone or other nontoxic material used for forming the outer barrier 445 protects the overlaid skin and blocks it from being damaged from harmful liquids including moisturizing water and/or exudating discharge 482. It is also to be noted that during fabrication, the inner barrier-surrounded dressing region R0 is kept dry due to presence of inner barrier 443 while one or more moisturizing liquids are selectively and controllably flowed into adjacent dressing region R1. The kept-dry, inner dressing region R0 may then by itself absorb a maximum amount of exudates when it is later applied to the corresponding wound 480 or it may do so with the assistance of an optionally attached extension part such as 270 of FIG. 2B. Water vapor 483A may readily evaporate out from the absorbed exudates 482 and escape into the ambient through unclogged portions of the permeation control layer 320 so as to make room for absorption of additional exudates into dressing region R0. In one embodiment, after the moisturizing clean liquid(s) is/are deposited into dressing region R1 with a computer-controlled selective dripper similar to tool 401, surface 431 of the patterned dressing layer 431 is covered with a peel-off wax paper or impermeable plastic sheet that traps the clean liquid(s) in dressing region R1 until the custom dressing 409 is about to be applied to its corresponding wound 480. If such a peel-off sheet is included in the packaged product (see FIG. 2), the corresponding dressing usage instructions will typically include an instruction to remove the peel-off sheet prior to application to the corresponding wound 480.

FIG. 4B additionally shows the inner liquid transfer portal 425B that was cut through layer 315 of FIG. 3A and represented by example 325B. Exudate 481 that is first absorbed by hydrophilic layer 430' may flow out through portal 425B for absorption by an attached dressing extension part such as 270 of FIG. 2B. The attached extension part 270 (e.g., attached by pressure activated adhesive dots, not shown) typically has an absorption capacity much larger than that of region R0 of custom layer 430'. Accordingly, design of the dressing is not limited the limited dimensions of region R0 of custom layer 430'.

Referring to FIG. 2B, custom dressing part 209' is removed from its sterile packaging 206/207/208 and applied to the corresponding open wound. One or more extension parts such as 260 and 270 are removed from their corresponding sterile packagings (not shown, but similar to 206/207/208) and attached to the custom dressing part 209' so as to thereby form a composite dressing system 290 having a custom fabricated part like 209' and standard or semi-customized extension parts like 260 and 270. The attachment of parts 260 and 270 to part 209' may take place before or after custom dressing part 209' is applied to the wound. A liquid sourcing extension part such as 260 may be partially or fully prefilled with its corresponding liquid when delivered inside its corresponding packaging (not shown, but similar to 206/207/208) or it may be filled with sourcing liquid (e.g., water, medicine, vitamins, etc.) after removal from its packaging but prior to attachment to custom part 209'. Dressing application instructing information such as 204e of FIG. 2A may provide the detailed information as to what course of action is to be taken with each patient, each wound and each corresponding dressing assemblage 290 on a given application date (204d).

Mating and attachment of extension parts such as 260 and 270 to custom part 209' may take on various forms. Generally, each extension part (e.g., 260, 270) will have a marked region covered by removable wax paper or the like which forms the liquid transfer portal of that extension part and corresponds to a matching liquid transfer portal such as 225A, 225B on the custom dressing part 209'. These may be color coded so that the care giver is less likely to make mistakes. In other words, portal 225A on part 209' may be surrounded by a green pigmentation and the corresponding portal area 264 on extension part 260 may be surrounded by a same green pigmentation and/or covered by a peel-away wax paper having the same green pigmentation. By contrast, portal 225B on part 209' may be surrounded by a red pigmentation and the corresponding portal area 274 on extension part 270 may be surrounded by a same red pigmentation and/or covered by a peel-away wax paper having the same red pigmentation. Thus the caregiver is alerted as to which extension part portal mates with which counterpart portal on the custom dressing part 209'. Concomitant with mating of each extension part portal (264, 274) to its custom part portal (225A, 225B), a bottom adhesive layer on each extension part may be exposed by removing a peel-away wax paper or the like and the exposed bottom adhesive layer (not explicitly shown) then bonds the bottom surface of the extension part (260, 270) to a corresponding top surface area of the custom dressing part 209'. Alternatively or additionally, breathable-through medical adhesive tape or the like may be used to bind the extension parts and custom part to one another and/or to the wound site area so as to form the assembled composite dressing 290.

Since the extension parts (e.g., 260, 270) typically attach to the top surface of custom part 209', there will often be a gap or space between surrounding skin and the bottoms of the extension parts which extend beyond the peripheries of custom part 209'. This gap may be filled with spacer foam such as is represented by 280. The illustrated height of the spacer foam is less than the illustrated height of custom part 209' but is understood in practice to match or slightly exceed the actual height of custom part 209'. A shorter height is shown so as not to obstruct some of the reference numbers in the drawing. The spacer foam 280 may be composed of any safe-for-skin porous and resilient material that allows the covered skin to breathe (so to speak) while preventing a pressure hot spot from appearing due to the elevation differences between custom part 209' and the extending beyond part of extension part 270. Examples of safe-for-skin porous foams include foams made of solid but flexible silicones and foams made of flexible polyurethane. The foam or other porous material interiors described herein for the extension parts should be sufficiently flexible to comfortably conform with the shapes of a patient's body parts. The outer edge of spacer foam 280 should be beveled (e.g., 45°) so as to prevent a pressure hot spot (a discontinuity in pressure applied to the skin) from appearing there too. The top surface of the spacer foam 280 should be adhesively bondable to the bottom of extension part 270 with the same adhesive used to bond extension part 270 to the top of custom part 209'. Thus portions 270, 280 and 209' of the assemblage 290 can be integrated together with use of singly adhesive layer (not shown) provided on the bottom of extension part 270. It is to be understood that another, similar spacer foam like 280 may be provided under extension part 260 for the same purpose. Spacer foam sheets of a thickness matching or slightly exceeding the thickness of custom part 209' may be provided with straight and curved perforations defined therethrough so that spacer foam sections roughly matching the peripheral contours of custom part 209' may be easily torn off by a care giver and positioned adjacent to the peripheral contours of custom part 209' before the extension parts (e.g., 260, 270) are finally glued or otherwise fastened into place. In one embodiment, the spacer foam sheets having periodic but spaced apart dots of skin-safe adhesive on their bottoms covered by a peel-away wax paper or other sheet so that after their peel-away sheets are removed, they may be adhesively attached to intact skin around the open wound and kept there before the extension parts (e.g., 260, 270) are attached.

As seen in FIG. 2B, the extension parts (e.g., 260, 270) of one embodiment are formed with beveled edges at their peripheries similar to the beveled periphery of spacer foam 280 so as to reduce the chance of creating pressure hot spots. If an extension part does not have a beveled periphery, that function may be provided by placing a beveled spacer foam (280) below the non-beveled extension part. In one embodiment each of extension parts (e.g., 260, 270) includes porous foam (e.g., 262, 272) in its interior. Examples of usable porous foams include foams made of solid but flexible silicones and foams made of flexible polyurethane. Other porous and flexible materials may be used instead. The purpose of the porous interior 262 of first extension part 260 is to store and output a pre-specified liquid (e.g., clean water, saline solution, medicine, etc.) for time released transfer through portals 264 and 225A into a barrier enclosed region of layer 230. From this barrier enclosed region, the sourced liquid may flow through wicking layer 240 (on the inner side of skin protecting barrier 245) to irrigate a corresponding and pre-characterized, pre-mapped zone of the underlying wound. The irrigating liquid flow is represented schematically in FIG. 2B as flow 105 and may for example flow next into an overly dry part of epitheliating wound zone 128 of FIG. 1 (or zone 292 of FIG. 2A).

Because the porous interior 262 of first extension part 260 stores a prescribed volume of a pre-specified liquid (e.g., water), it is undesirable to lose part of that stored volume to evaporation. As such, the first extension part 260 has a vapor impervious outer skin 265. The vapor impervious outer skin 265 may be composed of a vapor impermeable polyurethane film formed around (e.g., melted onto, laminated to, etc.) the exterior of the porous interior 262 or of any other vapor impermeable, flexible and skin-safe material that can provide similar functions. The vapor impervious outer skin 265 is discontinuous at least at the location where extension portal 264 mates with custom portal 225A so that the stored liquid (in 262) can flow out through extension portal 264. The vapor impervious outer skin 265 is preferably made of a safe-for-skin nontoxic polymer and is preferably kept spaced apart from underlying skin by a spacer foam such as 280 so that the underlying skin does not suffocate from direct and constant contact with the vapor impervious outer skin 265 of extension part 260.

The purpose of the second extension part 270 is, in contrast to the purpose of extension part 260, typically to absorb as much exudates or another liquid as possible. The porous interior 272 of extension part 270 may be made of a foam or other flexible porous material (e.g., a microfiberous material) that has great absorption capacity. It is possible for porous interiors 272 and 262 to be made of same foam material in one embodiment. However, the outer skin 275 of the second extension part 270 is preferably a vapor passing, although liquid impermeable material so that vapors or gases from the soaked up liquid may outgas into the ambient to thereby provide additional liquid absorption volume in the second extension part 270 as time progresses. The outer skin 275 of the second extension part 270 may be composed of a flexible silicone with liquid blocking pores or of a microfiberous material with liquid blocking pores, where the pores prevent discharge of microbe contaminated components of absorbed exudates but allow water vapor to dissipate outwardly. Exudate 141' and/or liquids that are to be soaked up by the second extension part 270 can flow up through a barrier enclosed section (e.g., the thinner part of the funnel 243) of the custom dressing part 209', out through custom portal 225B and into extension part portal 274. The volume of extension part 270 provides an absorption and storage volume for the nonvaporizable components of the up taken exudates. The exposed surface area of extension part 270 provides an offgassing surface area for offgassing gases from and vapors of vaporizable components of the up taken exudates.

Referring to FIG. 2C, shown is a system 295 of variably interconnectable extension parts in combination with a plurality of custom wound dressings, 209" and 209'". This drawing is not to scale. In one embodiment, each of the illustrated extension parts has the general shape of a rectangular prism or of an elongated ovaloid (whose top plan view is an oval and side plan view is a rectangle). The custom dressing parts of course have custom shapes and/or dimensions. A first of the extension parts, 260A is connectable at both its top and bottom major surfaces respectively to bridge extension part 268AB and to first custom wound dressing 209". In one embodiment, the porous interior and outer skin of the first top/bottom connectable extension part 260A respectively correspond to those of liquid sourcing part 260 of FIG. 2B. In an alternate embodiment, the porous interior and outer skin of the first top/bottom connectable extension part 260A respectively correspond to those of liquid absorbing part 270 of FIG. 2B.

Prior to assembly with other parts, each of the connections portals, e.g., 264A and 264aa of each T/B connectable extension part like 260A and of each T/T mid-part like 260B and of each bridging part like 268A is covered with a peel-away and adhesive uncovering sheet (e.g., wax paper) like 266A (shown in phantom). When the portal's peel-away and adhesive uncovering sheet is peeled away, it exposes the respective portal and an adhesive layer therearound. The exposed adhesive layer may then be used to bond to another part. Portal 264aa is shown as already aligned with and sealingly bonded to portal 269a of bridge extension part 268AB such that a contained liquid may be transferred through these portals with substantially no leakage. On the other hand, portal 264A is shown as aligned with but not yet sealingly bonded to corresponding portal 225A" of custom dressing part 209". It is understood that peel-away and adhesive uncovering sheets 266A and 267A will be peeled away so that the first top/bottom connectable extension part 260A can be securely bonded at its bottom surface after a user has placed T/B part 260A at a desired convenient orientation (e.g., angle) relative to the first custom dressing part 209". Thereafter, the hydrophilic microfibers layer 230" of the custom dressing will be in fluid communication with the foam interior of the first top/bottom connectable extension part 260A such that extension part 260A can supply a substantial volume of irrigating liquid to custom part 209" without any substantial leakage at the junction of portals.

If the irrigation supply capacity needs to be increased, this can be conveniently done by adding bridge part 268AB and either of T/T or T/B extension parts 260B or 260C thereto. It is understood that prior to assembly, the first bridge part 268AB has two peel-away and adhesive uncovering sheets like 266A at its respective bottom surface portals and optionally two more peel-away and adhesive uncovering sheets like 267A covering opposed halves elsewhere on its bottom surface. Thus bridge part 268AB may be first aligned and adhesively bonded to T/B part 260A and thereafter a next-to-be-linked part like 260B or 260C may be positioned as desired prior to its adhesive bonding to bridge part 268AB. Note that in one embodiment, a gap is provided between the edges of the connectable extension parts so that they can be easily rotated relative to one another to thereby form a linear array of such extension parts, or a snake like formation, or a tubular formation around an arm or leg, or a spiral or helical formation, and so forth. The spatial orientation of linked together extension parts may vary to suit peculiarities of each unique wound site, surrounding intact skin, surrounding body topography and patient situation.

In the illustrated example of FIG. 2C, the caregiver (or dressing system designer) has elected to link a T/T connectable middle extension part 260B to first bridge 268AB and to use a second bridge 268BC for linking middle extension part 260B so as to be in fluid communication with a second T/B extension part 260C. Moreover, the user has elected to open bottom portal 264C of extension part 260C and bondingly mate it to portal 225A" of a second custom dressing part 209'". Thus in this case, one continuum of liquid sourcing extension parts: 260A, 260B, 260C provides irrigating liquid to both of the first and second custom dressing part 209" and 209'". Any of a variety of configurations may be formed as desired by the user and/or prescribed by the dressing designer or doctor. In one embodiment, all bridging parts (268AB, 268BC, etc.) have gas impermeable outer skins so that they may be universally used with liquid sourcing extension parts (like 260) as well as liquid absorbing extension parts (like 270). In an alternate embodiment, some bridging parts may have gas permeable outer skins so that they may provide additional surface area for exhausting water or other vapors while blocking microbes or other solid particulates from escaping.

By way of an example of how the variably linkable extension parts of FIG. 2C may be used, a diabetic patient may have a heavily exudating wound on his foot which needs significant and constant irrigation with clean moisturizing fluid as well as significant uptake of infected exudates. The prescribing doctor may design two linear arrays of linked extension parts extending up the patient's leg from the wound site an the custom dressing provided thereat. A first of the taped-to-leg and linear arrays contains a corresponding volume of irrigating liquid that is to be sourced to wound over the course of a treatment period while the second array provides sufficient uptake capacity to absorb the predicted amount of exudates that is expected to emerge from the wound. Thus, after the custom dressing and its attendant array(s) of linked-together extension parts are assembled and applied to the wound, the caregiver may step away and not worry about minute-to-minute attendance to the wound layer sufficient irrigation and absorption capacities have been provided to automatically treat the wound in a customized manner over a predefined treatment period. this frees the caregiver to attend to other patients while providing the given patient with continuous heal-promoting treatment for his unique wound (e.g., 120 of FIG. 1).

Figure 5A:
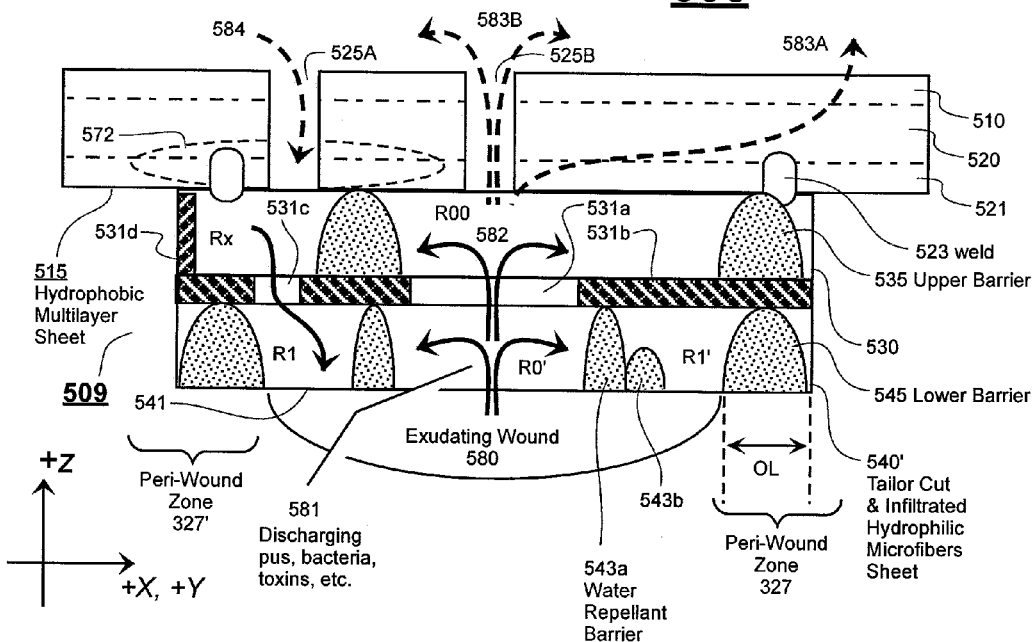
FIG. 5A is a side sectional view showing how fluid blocking barriers may be formed in multiple layers of hydrophilic absorbent sheets so as to direct flow of different fluids to or from pre-identified and pre-characterized wound zones and also to and from external extension parts.
Figure 5B:
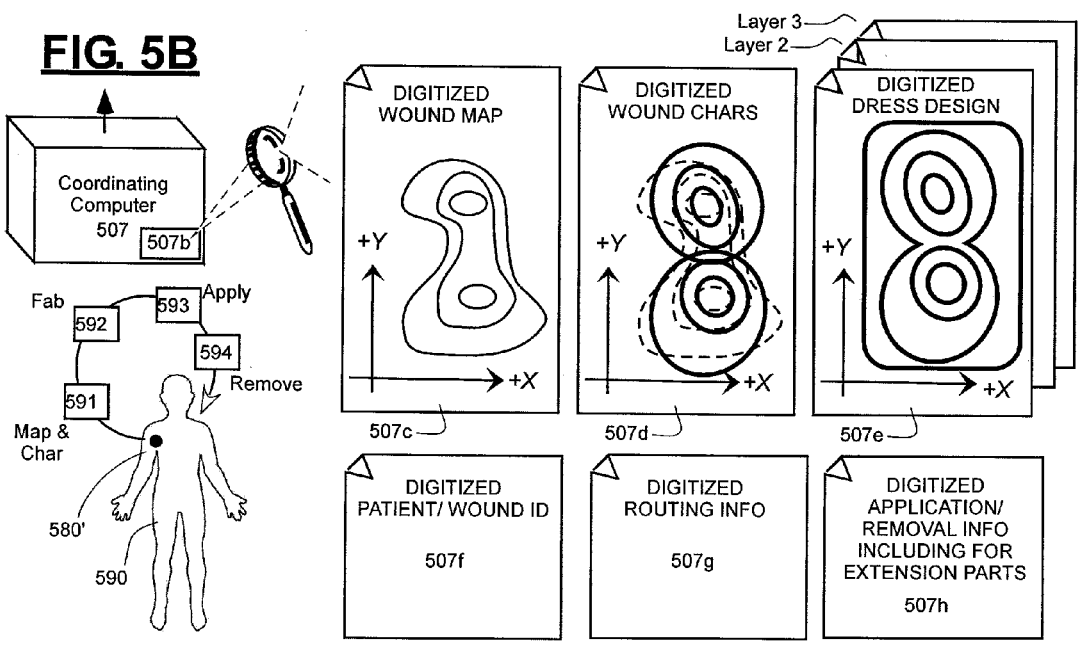
FIG. 5B is a schematic for showing how a coordinating computer program executing across a network or in a particular computing machine can assure a complete circle of coordination for customized dressing creation and usage, from wound mapping and characterization, to custom fabrication of matching dressing parts and subsequent routing of the fabricated dressing parts for application to the correct wound on the correct patient.

Referring next to FIG. 5A, shown is a side sectional view that illustrates how relative to the introductory configuration of FIG. 4B, yet more complex fluid routing and/or blocking barriers may be formed within multiple layers (e.g., 530, 540) of hydrophilic absorbent sheets in a wound dressing product 500 so as to direct flows of different fluids to or from pre-identified and pre-characterized wound zones and to or from attached extension parts (not shown) via respective extension portals (e.g., 525A, 525B). Here, a second hydrophilic fibrous layer 540 is cut, deposited, fastened on (e.g., spot welded on) and patterned after a previous hydrophilic layer 530 has been cut, deposited, fastened on (e.g., spot welded on) and patterned in accordance with computerized first hydrophilic layer defining data (see briefly 507e of FIG. 5B). The bulk material of the second hydrophilic fibrous sheet section 540 may be the same as or different from the bulk material of the first hydrophilic fibrous sheet section 530. In the automated patterning of the first sheet section 530, an upper and close bounded water repellent barrier 535 is deposited and somewhat fixedly embedded into the thickness of porous layer 530 as shown. Region R00 is designated by a corresponding computer-readable data structure (507e) as having the function of absorbing exudate 582 that enters into layer 530 while region Rx is designated by the corresponding computer-readable data structure (507e) for donating late stage moisture and/or a prescribed medicine. After the water repellent material of upper barrier 535 has been embedded into layer 530, a patterned and fluid impermeable film 531b, 531d is formed on the −Z facing major surface of layer 530 and optionally (as in the case of 531d) around its peripheral edge by for example depositing a hardenable polymer film material or by melting selected parts of the −Z facing major surface (531) of layer 530 at desired positions. This selective patterning of the −Z facing major surface of layer 530 leaves liquid and/or gas permeable passageways 531a and 531c on that surface and between the first and second layers 530, 540 while locking the upper peripheral water repellent barrier 535 in place. Optionally, open liquid passageway 531c is then used for infusing clean water or saline solution and/or a liquid medicine into region Rx of the first hydrophilic layer 530 before next layer 540 is attached. Alternatively, the supplied clean water or other treatment liquid 584 is supplied from one or more extension parts (not shown) that are in fluid communication with irrigation receiving portal 525A. Although in one embodiment, the laterally extending barriers 531b, 531d to liquid and/or gas flow are formed by deposition of an impermeable film laterally on the −Z face of layer 530, such laterally extending barriers could additionally or alternatively be custom shaped, dimensioned and formed by selective deposition and embedding of a water repellant viscous liquid that only partially penetrates into the thickness of layer 530 similar to the way that selectively deposited liquid region 543b (described below) only partially embeds into the thickness of next-described layer 540.

After patterning of layer 530 is substantially complete, the second hydrophilic sheet section 540 is then shaped and dimensioned (e.g., by custom cutting with tool 301 for example) and attached (e.g. spot welded to layer 530—welds not shown). Thereafter lower water repellent barriers 545 and 543a are selectively embedded fully through the thickness of layer 540 as shown. Optionally, a less viscous and thus more readily spreadable silicone or other water repellent liquid 543b is deposited into region R1' of layer 540 just before water or another moisturizer is selectively infused into region R1'. The viscosity of this more readily spreadable but water repellent liquid 543b is such that were it not for the water (or other moisturizer) consuming the remaining volume of region R1', the readily spreadable repellent liquid 543b would over a relatively short period of time (e.g., 15-30 minutes) begin to spread out over region R1' and close off its bottom surface area (541) rather than retaining its shape as relatively fixedly as do barriers 535 and 543a. However, the water (or other moisturizer) that is quickly infused into region R1' after readily spreadable repellent liquid 543b has been infused, pushes the readily spreadable repellent liquid 543b up against less spreadable barrier 543a and prevents 543b from spreading out laterally as long as there is sufficient aqueous liquid present in dressing region R1' to push against readily spreadable repellent liquid 543b. On the other hand, during end stage use of custom dressing 509 on corresponding wound 580, the aqueous liquid in dressing region R1' substantially runs out and then spreadable repellent liquid 543b spreads out across the wound interfacing surface 541 of dressing region R1' to thereby close off region R1' and block moisture from being absorbed from the wound into the substantially dried out region R1'. In this way, the custom dressing 509 dynamically adapts itself to changed conditions and keeps an epitheliating wound zone (not shown) under region R1' from drying out.

While frusto-elliptical section 543b has been described for one embodiment as being composed of a readily spreadable embedded hydrophobic liquid, in an alternate embodiment it constitutes a more fixedly embedded hydrophobic liquid that provides one or more functions including that of reducing the water-permeable surface area by way of which region R1' interfaces with the underlying wound 580 or defining a water-permeable passageway of desired thickness between the top of frusto-elliptical section 543b and a spaced apart horizontal barrier such as the illustrated 531b. In both instances, the rounded top of frusto elliptical section 543b does not need to abut with water-impermeable horizontal barrier 531b or with the bottom of a water-impermeable layer such as 520. In other words, when it is formed, the frusto elliptical section 543b does not have to infiltrate all the way through the thickness of its supporting dressing layer 540. Depth of penetration by the precursor material (e.g., 401a) of frusto elliptical section 543b into layer 540 can be varied by adjustment of the heating temperature used to cause the precursor material (e.g., 401a) to infiltrate vertically into layer 540 or by the adjustment of heating time (for material 401a or for a volatile solvent mixed with it) or by the volume of precursor material (e.g., 401a) deposited as a drop on surface 541. When frusto elliptical section 543b serves as a baffle for reducing water-permeable space between its +Z top and an overhanging horizontal barrier (e.g., 531b), it may be used to controllably limit the flow rate of an aqueous liquid from one compartment in the dressing to another (including liquid supplied by or taken up by external extension parts) by controlling the distance between its +Z top and the overhanging horizontal barrier (e.g., 531b).

It is to be understood from the above that the present disclosure is not limited to just depositing water repellent liquids to form static and/or dynamic barriers in the custom dressing part. Dynamic barriers may also be provided in the extension parts, for example so that a dried out liquid supplying part automatically closes off from a linked chain after having dispensed its load of clean liquid. Viscosity may be adjusted for different barriers, for example by selectively depositing different silicones of different viscosities and optionally mixed with nonvolatile solvents so as to provide relatively static barriers in some locations of a given dressing layer and so as to provide relatively dynamic, more easily spreadable barriers in selected other locations of a given dressing layer or an extension part. While only frusto elliptical section 543b has been described in one version thereof as being readily diffusible through regionR1' of layer 540, a same tactic could have been used in other dressing regions Rx and R1 of FIG. 5A by infusing readily spreadable repellent liquids like 543b in respective regions Rx and R1 just before those regions are respectively filled with respective aqueous liquids (e.g., a medicine in region Rx and saline solution in region R1). Then as the respective aqueous liquids run out from their storage compartments in the dressing (or an external extension part), the dynamically spreadable barriers (not shown) in regions like Rx and R1 would spread out to close off those regions during late stage usage of the dressing 509 and would prevent undesired drying of the underlying wound zone. Note that melt zone 572 in layers 520-521 caps most of the Rx region of layer 530 (except for portal area 525A) and thus prevents the Rx region of layer 530 from drying out quickly due to undesirable outgassing through layer 520.

Additionally, since upper region R00 of layer 530 has been kept dry by operation of upper barrier 535 and since upper region R00 is not capped by an out-gas blocking film above it, the upper region R00 of layer 530 is available to absorb large amounts of exudates from region R0' of lower liquid 540 and to readily dissipate water vapor 583A via the enlarged upper surface area of upper region R00. Moreover, with addition of optional extension parts (not shown) to portal 525B, a further volume 583B of the exudate flow can be taken up by the extension parts and their increased surface areas may also be used for vapor dissipation. In other words, the vapor dissipation surface area of the upper part (in the +Z direction) of dressing region R00 is not constrained by dimensions of underlying wound zones as much as the wound interfacing layer 540 may be. With use of vertical barriers like 543a and horizontal barriers like 531b, funneling structures may be devised for expanding the water vapor dissipating surface area made available for a given one or more wound zones and for providing sufficient area to include interface portals for interfacing with external extension parts. Accordingly, when custom dressing 509 is applied to wound 580, exudate flow 581 is absorbed not only into region R0' of lower layer 540 but rather it continues to migrate upwardly, passing through the intentionally left open liquid passageway 531a and then spreading out laterally into wider region R00 of upper layer 530 and yet further through portal 525B to be absorbed by one or more liquid absorbing extension parts. Note that the wider lateral area of region R00 means that it has greater volume (assuming layer 540 is not thicker than layer 530) and thus can absorb aqueous liquids at a faster rate and evaporate off water vapor 583 at a faster rate form its larger upper surface area. The availability of patternable vertical barriers like 535, 545, 543a, etc. and patternable horizontal barriers like 531b and 572 and of extension parts and extension portals like 525A, 525b give designers of automatically fabricated custom wound dressings an enlarged number of options by way of which they can control directions, rates and timings of liquid flows going into a given wound (e.g., medicine Rx) and liquid flows moving out of the given wound (e.g., exudates 581). Additionally, by providing more readily spreadable barriers such as 543b within one or more dressing layers, designers can define dynamically closeable passageways which close up after a corresponding liquid content has run dry. Thus a wound dressing can be designed to dynamically adapt to changing conditions and to provide custom tailored treatment over prolonged periods of time.

Referring to schematic diagram 5B, it is to be appreciated that a single coordinating computer program 507b can be executing either in a corresponding single coordinating computer 507 or across a plurality of networked processors (e.g., of a network cloud, not shown) so as to assure that a matching custom dressing (e.g., 509 of FIG. 5A) is correctly fabricated for a given individual and pre-mapped wound (e.g., 580, 580') and that the same matching custom dressing as well as optional, attachable extension parts (e.g., 260, 270 of FIG. 2B) are automatically packaged in respective sealed packages, that the dressing and extension part containing packages are automatically labeled so as to be appropriately routed (593) after fabrication (592) to the same individual wound (e.g., 580') for assembly thereat (if extension parts are used) and application to the wound over a physician-prescribed time duration and with appropriate inclusion of irrigation by saline or other liquids if so prescribed. In other words, a full circle of control and coordination may be provided from the time of wound mapping and characterization (591) to the time of dressing assembly and application (593) and the time of dressing removal (594) and discard. To do so, the coordinating computer program 507b may logically interlink a plurality of data files or other data structures including but not limited to: a digitized wound map or image 507c of the specific wound (which map corresponds to a predefined physical reference frame such as one formed by specific X and Y coordinates on the patient's body); digitized wound characterizing maps and/or plots 507d (see also FIGS. 1B-1D); digitized, layer by layer, dressing design maps 507e including optional digitized design maps showing how extension parts are to be coupled with one or more custom dressing parts; digitized patient identifying and wound identifying data 507f; digitized routing data 507g for defining how the fabricated dressing parts (e.g., custom dressing parts and optional extension parts) are to be routed to the patient (e.g., via an identified doctor and/or nurse) after fabrication, packaging and compilation thereof is complete; and digitized application and/or removal information 507h for defining when and/or how the corresponding custom dressing (509) and optional extension parts (e.g., 260A-C, 270, 280) are to be applied to the corresponding wound, and when and/or how the corresponding custom dressing (509) with its extension parts (e.g., 260, 270) are to be removed from corresponding wound.

It is to be understood that the digitized patient identifying and wound identifying data 507f may be used multiple times including for associating the digitized wound image 507c with the actual wound, for associating the automatically fabricated dressing 509 and optional extension parts with the actual wound; and for printing out or otherwise generating routing data 507g that causes the packaged product(s) to be correctly aggregated and ultimately routed to the same actual wound 580'. In one embodiment, the digitized patient identifying and wound identifying data 507f and the digitized routing data 507g are formed as computer data files at substantially the same time and in substantially the same location as the digitized wound map or image 507c is created (and generally by a same person for all three files) so that the wound map or image 507c is correctly attached or otherwise logically associated with and tied to the patient identifying and wound identifying data 507f and to the routing data 507g from the point of inception of the wound image. This minimizes the risk that a wrong custom dressing will be applied to a wrong wound or even a wrong patient or not properly or timely delivered to the patient due to accidental mix up of one or more of these pieces of functional information.

The digitized wound characterizing maps and/or plots 507d and corresponding treatment plans (which could be digitized text notes appended to the wound zone characterizing maps) are typically generated by a doctor or other skilled health care providing professional(s) at the same time (and/or same place) that the digitized application and/or removal information 507h is generated so that the two files (507d, 507h) correctly correlate with one another. The latter two files (507d, 507h) are then appended to or otherwise logically connected to at least the digitized patient identifying and wound identifying data 507f and the digitized routing data 507g. In one embodiment, the digitized wound characterizing maps and/or plots 507d delineate skin zones and/or other zones that are to be protected from exposure to exudates or other tissue harming substances by use of one or more fluid containment barriers such as for example those made with embedded viscous silicones or the like. In one embodiment, digitized wound site characterizing maps and/or plots 507d delineate skin zones around the wound and/or other zones that are to be protected from having dressing extension parts adhered to them (for whatever reason, i.e., patient hyper sensitivity at those spots, etc.). In one embodiment, the digitized wound identifying data 507f includes data identifying and locating on the identified patient, a frame of reference (e.g., corresponding to X/Y frames shown in FIG. 5B) relative to which the custom wound dressing and/or its optional extension parts are to be oriented and identifying the prescribed orientations of the custom dressing part (e.g., 509) and its associated extension parts (e.g., 260, 270) if any.

The digitized routing data 507g may include an audit trail that identifies the doctor(s) or other skilled health care providing professional(s) who characterized the wound zones and the adjacent skin areas that may need protection, and who created the treatment plan. The routing data 507g may also identify the doctor(s), nurse(s) or other skilled health care professional(s) who are delegated the task of align-wise applying the custom wound dressing and its optional extension parts to the identified wound site and/or removing the wound dressing from the identified wound at the treatment prescribed appropriate times. In one embodiment, the coordinating computer 507 automatically obtains the availability schedules of the dressing applying caregiver (e.g., a home visiting nurse) and integrates the same into the design of the custom dressing and its extension parts (if any) so that wound irrigation may be continuous between sequential dressing changes to be made at the scheduled availability times of the caregiver. In other words, if a nurse can see the patient every 4 hours, this would automatically call for one size for the custom dressing and its extension parts (if any) whereas if the nurse can see the patient only once every 24 hours this would often automatically call for a substantially larger capacity for liquid sourcing and liquid sinking extension parts due to the prolonged time between visits. Accordingly, the composite wound dressing (290 or 295) is automatically designed to not only custom fit the targeted wound but to also custom fit the available care giver schedule available to the given patient. All these factors minimize the risk that a wrongly shaped, dimensioned or otherwise formulated dressing will be designed, fabricated and applied to a wrong wound or even a wrong patient or not properly or timely delivered to the patient with sufficient irrigation or absorption capacities or not properly removed from the wound due to accidental mix up of one or more of these pieces of functional information regarding routing and responsibility for data management and for use of the associated custom wound dressing (and optional extension parts) or the packaged products that include the custom wound dressing and its associated extension parts, if any. Since in one embodiment the responsible people are so-identified by a file kept in a database and logically associated with the identified patient and identified wound, a game of finger pointing cannot be later played so as to escape responsibility regarding who had the responsibility to make sure the right custom dressing is correctly applied to the correspondingly matching wound at the appropriate time with sufficient irrigation and/or liquid drainage capacities and thereafter removed at an appropriate time.

The digitized dressing design maps (including those for extension parts) 507e can be generated in automated response to the digitized wound characterizing maps and/or plots 507d and corresponding treatment plans or they may be generated by a skilled dressing designer with automated assistance provided by a computer (e.g., 507) that suggests to the dressing designer what shapes, sizes and materials should be picked for each dressing layer, how many dressing layers should be used for each treatment function, how vertical and/or horizontal fluid containment barriers (e.g., 543a, 543b, 545, 531b, 572) should be shaped, dimensioned, located and formed of respective fluid containing materials in or between the various dressing layers and which and how many extension parts should be used in combination with the custom dressing. It is therefore understood that the digitized dressing design maps 507e can include specifications for the shapes, dimensions, locations and/or fluid containing materials to be used for forming respective vertical and/or horizontal fluid containment barriers (e.g., 543a, 543b, 545, 531b, 572) within or on the surfaces of the various custom dressing layers and additional specifications for extension parts (e.g., 260, 270) that are to be operatively coupled to the custom dressing part (e.g., 509). In one embodiment, the digitized dressing design maps 507e include specifications for the shape, dimensions, locations and/or barrier forming materials to be used for protecting adjacent skin from harmful substances such as is done for example by lower barrier 545 of FIG. 5A. In one embodiment, the digitized dressing design maps 507e also include specifications for the shape, dimensions, locations and/or interior-exterior forming materials of extension parts that are to be operatively coupled to the custom dressing part (e.g., 509). The digitized dressing design maps 507e may further include information regarding amounts, locations, and identities of one or more prespecified liquids (e.g., water, saline solution, peroxide, antiseptics, etc.) that are to be applied to prespecified liquid containment areas of the customized wound dressing part and/or its associated extension parts as each of these is removed from its respective sterile package (e.g., 206/207/208) and handled prior to application of the composite dressing (e.g., 290) to a corresponding wound site.

It is also to be understood that the digitized dressing design maps 507e may be appended to otherwise logically associated (e.g., in a relational database) with one or more of the other data files 507c-507d, 507f-507h and that the digitized dressing design maps 507e may be used for controlling automated fabrication (592) of the corresponding custom wound dressing 509 and for automated logical association of the custom wound dressing with extension parts if necessary. Identification of the person or persons respectively responsible for generating the digitized dressing design maps 507e and for responsively fabricating the corresponding wound dressing 509 and aggregating it with associated extension parts (if any) may be appended into the digitized routing data file 507g at the times of respective dressing design, custom dressing fabrication and dressing parts aggregation. The unique identification number (e.g., Rx number, not shown) that is optionally included on label 204 may be submitted, in one embodiment, to a relational database (e.g., one implemented in computer 507) after the custom wound dressing is fabricated and all of files 507c-507h contained therein may be responsively retrieved for review and evaluation. The relational database may include additional files or records that logically tie to the unique dressing identification number (e.g., Rx number, not shown) and that indicate how well the patient responded to the automatically designed and automatically fabricated custom wound dressing 509 and/or to medicines or other substances added thereinto directly and/or by way of attached extension parts.

The present disclosure is to be taken as illustrative rather than as limiting the scope, nature, or spirit of the subject matter claimed below. Numerous modifications and variations will become apparent to those skilled in the art after studying the disclosure, including use of equivalent functional and/or structural substitutes for elements described herein, use of equivalent functional couplings for couplings described herein, and/or use of equivalent functional steps for steps described herein. Such insubstantial variations are to be considered within the scope of what is contemplated here. Moreover, if plural examples are given for specific means, or steps, and extrapolation between and/or beyond such given examples is obvious in view of the present disclosure, then the disclosure is to be deemed as effectively disclosing and thus covering at least such extrapolations.

By way of example, it is understood that the configuring of a coordinating computer (e.g., 507 of FIG. 5B) in accordance with the disclosure can include formulation of algorithms that take advantage of the ability to form custom patterned vertical and/or horizontal barriers for one or more layers of a multi-layer custom dressing and take advantage of the ability to extend the capacities of compartments in the custom dressing part with use of extension parts. As such, machine executable instructing signals may be stored in a functional storage of a computer to cause the computer to determine one or more barrier defining parameters including but not limited to: which of plural barrier forming liquids to use, where to deposit the selected barrier forming liquids and to what depth; what order to deposit the selected barrier forming liquids in; what temperature to heat the deposited barrier forming liquids to if at all; what overlying or underlying horizontal barriers to form adjacent to the vertical barriers; and so forth. The so stored, machine executable instructing signals may also cause the same or another computer to determine which and how many (if any) extension parts are to be operatively coupled to the custom designed and custom fabricated dressing. A computer-readable medium (e.g., 507b) or another form of a data storage product (including but not limited to, a hard disk, a compact disk, a flash memory unit, a downloading of manufactured instructing signals over a network and/or the like may be manufactured and used for defining one or more data structures for custom fabricating a custom wound dressing (including attaching thereto of extension parts) for a corresponding individual wound where the data structures include one or more of a wound zones map, a wound zones characterizing map, layer by layer dressing design maps, patient and wound identification data, dressing routing data and dressing usage data; where the data structures are logically linked to one another to thereby verify that not only a correct custom dressing and its optional extension parts are automatically aggregated for application to a given wound, but that the fabricated custom dressing part(s) and its/their optional extension parts are thereafter timely routed to the corresponding wound and correctly assembled thereat.

RESERVATION OF EXTRA-PATENT RIGHTS, RESOLUTION OF CONFLICTS, AND INTERPRETATION OF TERMS

After this disclosure is lawfully published, the owner of the present patent application has no objection to the reproduction by others of textual and graphic materials contained herein provided such reproduction is for the limited purpose of understanding the present disclosure of invention and of thereby promoting the useful arts and sciences. The owner does not however disclaim any other rights that may be lawfully associated with the disclosed materials, including but not limited to, copyrights in any computer program listings or art works or other works provided herein, and to trademark or trade dress rights that may be associated with coined terms or art works provided herein and to other otherwise-protectable subject matter included herein or otherwise derivable herefrom.

If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

Unless expressly stated otherwise herein, ordinary terms have their corresponding ordinary meanings within the respective contexts of their presentations, and ordinary terms of art have their corresponding regular meanings within the relevant technical arts and within the respective contexts of their presentations herein. Descriptions above regarding related technologies are not admissions that the technologies or possible relations between them were appreciated by artisans of ordinary skill in the areas of endeavor to which the present disclosure most closely pertains.

Given the above disclosure of general concepts and specific embodiments, the scope of protection sought is to be defined by the claims appended hereto. The issued claims are not to be taken as limiting Applicant's right to claim disclosed, but not yet literally claimed subject matter by way of one or more further applications including those filed pursuant to 35 U.S.C. §120 and/or 35 U.S.C. §251.

What is claimed is:

1. A custom wound dressing comprising:
    (a) a first layer configured to interface with a specific wound, the first layer comprising a hydrophilic material; and
    (b) a second layer comprising a liquid flow blocking material impermeable to fluid, wherein a opening is formed in the second layer for allowing liquid to flow through the second layer; and
    (c) a dressing extension part operatively coupled or couplable to the opening and comprising at least one of a porous solid foam and a porous microfiberous material.

2. The custom wound dressing of claim 1 wherein the dressing extension part includes:
    a corresponding porous interior that can source or can absorb a predefined liquid; and
    an outer skin covering the porous interior.

3. The custom wound dressing of claim 2 wherein the outer skin has at least an extension portal defined therethrough and structured to operatively couple with the opening of the custom dressing part for passing a liquid between said opening and said extension portal.

4. The custom wound dressing of claim 2 wherein the outer skin is impermeable to water vapor.

5. The custom wound dressing of claim 2 wherein the outer skin is permeable to water vapor but does not allow microbes or larger particles to pass through the outer skin.

6. The custom wound dressing of claim 1 further including:
    at least a custom positioned vertical barrier embedded in the wound interfacing layer for preventing or inhibiting a liquid absorbed by first layer from spreading laterally from one side of the first custom positioned vertical barrier to an opposed other side of the vertical barrier; and
    where the custom positioning of the vertical barrier corresponds to a positioning of at least one of pre-mapped wound zones.

7. The custom wound dressing of claim 6 wherein the custom positioned vertical barrier includes hydrophobic material that causes the vertical barrier to have water repelling properties.

8. The custom wound dressing of claim 7 wherein said hydrophobic material of the vertical barrier includes a silicone or a silicone oil having a viscosity in the range of 1 CentiStoke to 10,000 CentiStoke.

9. The custom wound dressing of claim 6 wherein the custom positioned vertical barrier essentially consists of a silicone or a silicone oil.

10. The custom wound dressing of claim 6 wherein the first layer is dimensioned to contact at least one of the pre-mapped wound zones and the custom positioned vertical barrier is positioned to circumscribe an interface area corresponding to the at least one pre-mapped wound zone.

11. A combination of a first package and a first custom wound dressing part enclosed in the first package, where the first custom dressing part is configured for interfacing with a first prespecified external extension part, where the first custom dressing part is further configured for treating a specific wound identified by first indicia that is at least logically coupled to the first package, where the specific wound has pre-mapped different wound zones, and where the first custom dressing part comprises:
    (a) a plurality of layers extending laterally in the first custom dressing part, including a first layer having a first porous material; and
    (b) among said plurality of laterally extending layers, at least a second layer composed of a liquid flow blocking material that blocks bulk liquid from flowing therethrough, where the second layer has at least a first custom portal opening defined therein for allowing a first bulk liquid to flow through the first portal opening while the first bulk liquid is in communication with the first layer; and where the first custom portal opening is operatively couplable to said first prespecified external extension part.

12. The combination of claim 11 wherein the first prespecified external extension part is enclosed in a second package.

13. The combination of claim 12 wherein the second package is logically coupled to at least one of the first package and specific wound by second indicia provided in association with the second package.

14. The combination of claim 11 wherein the first layer includes at least a first custom positioned vertical barrier embedded in the first layer for preventing or inhibiting a first liquid absorbed by the first porous material from spreading laterally from one side of the first custom positioned vertical barrier to an opposed other side of the first vertical barrier;
    and where the custom positioning of the first vertical barrier corresponds to a positioning of at least one of said pre-mapped wound zones or a pre-mapped skin zone adjacent to the wound.

15. The combination of claim 14 wherein the first custom positioned vertical barrier includes a substantial amount of a silicone or a silicone oil for causing the first vertical barrier to have hydrophobic properties.

16. The combination of claim 14 wherein the first custom positioned vertical barrier includes a mineral oil or a vegetable oil.

17. The combination of claim 14 wherein the first custom positioned vertical barrier includes a water repelling liquid having a viscosity in the range of 1 CentiStoke to 10,000 Centistokes.

18. The combination of claim 14 wherein the first layer is a wound interfacing layer that is configured to interface with the identified wound, and where the first vertical barrier circumscribes an interface area corresponding to one of the pre-mapped zones of the wound.

19. The combination of claim 14 wherein the first custom positioned vertical barrier includes a coloring dye.

20. The combination of claim 14 wherein the first custom positioned vertical barrier is positioned to align over the at least one pre-mapped adjacent skin zone and to protect the adjacent skin zone from exposure to harmful substances.

21. The combination of claim 14 wherein the first custom positioned vertical barrier is positioned to protectively align relative to the at least one premapped adjacent skin zone and to protect the adjacent skin zone from exposure to harmful substances.

22. The combination of claim 14 wherein the second of said plurality of laterally extending layers is a gas or vapor permeable porous and hydrophobic layer that is permeable in at least one region of the second layer by a predefined gas or vapor.

23. The combination of claim 22 wherein the second laterally extending layer has one or more custom patterned regions of comparatively reduced or essentially no permeability for the predefined gas or vapor in addition to having said at least one region exhibiting comparatively larger permeability to the predefined gas or vapor and wherein the one or more of the custom patterned regions correspond to zones of the identified wound.

24. The combination of claim 23 wherein a first of the custom patterned regions with reduced or essentially no permeability is positioned above the first custom positioned vertical barrier.

25. The combination of claim 23 wherein the second laterally extending layer contains intersecting nonwoven microfibers and said one or more custom patterned regions of comparatively reduced or essentially no permeability include corresponding films formed by melting of the microfibers.

26. The combination of claim 23 wherein the second laterally extending layer contains intersecting nonwoven microfibers and said one or more custom patterned regions of comparatively reduced or essentially no permeability include a laterally extending gas impermeable film deposited on the microfibers.

27. The combination of claim 23 wherein the second laterally extending layer contains intersecting nonwoven microfibers having an average pore size less than less than about 0.5 micron.

28. The combination of claim 11 and further comprising:
(c) within said plurality of laterally extending layers, a second layer having a second porous hydrophilic material whose bulk structure is the same as or different from that of said first porous hydrophilic material; and
(d) at least a second custom positioned vertical barrier embedded in the second layer for preventing or inhibiting a second liquid absorbed by the second porous hydrophilic material from spreading laterally from one side of the second custom positioned vertical barrier to an opposed other side of the second vertical barrier.

29. The combination of claim 28 and further comprising:
(e) between the first and second laterally extending hydrophilic layers, one or more laterally extending fluid barriers that are impermeable to a predefined liquid and/or impermeable to a predefined vapor or gas, and where there is at least one zone between the first and second laterally extending hydrophilic layers where the predefined liquid and/or predefined vapor or gas can flow between the first and second laterally extending hydrophilic layers.

30. The combination of claim 11 wherein said first package comprises:
(c) a first packaging sheet;
(d) a second packaging sheet, attached to the first sheet so as to enclose the first custom dressing part therebetween; and
(e) at least a first label integrally formed on or attached to one of said first and second packaging sheets and providing said indicia that identifies the specific wound.

31. The combination of claim 30 wherein the first said indicia includes a graphic or schematic of at least one of body anterior and body posterior and an indication of where on the represented body anterior or body posterior the identified wound is located.

32. The combination of claim 31 wherein said graphic or schematic includes an indication of what orientation the first prespecified external extension part and the first custom dressing part are to take relative to one another and/or relative to the identified wound and/or relative to the represented body anterior or body posterior.

33. The combination of claim 31 wherein the at least first label further provides second indicia separately identifying the patient having the identified wound.

34. The combination of claim 31 wherein the at least first label further provides second indicia indicating a route and/or method by way of which said combination of the first package and the first custom dressing are to be delivered to the identified wound or patient having the identified wound.

35. The combination of claim 34 wherein the second indicia further indicates how many and/or further indicates which extension parts are to accompany the first custom dressing and its associated first package on the indicated route or by way of the indicated method of delivery of the first custom dressing to the identified wound or patient having the identified wound.

36. The combination of claim 30 wherein the at least first label provides indicia indicating at least one of a prescribed date for application or prescribed date for removal of the first custom dressing part and its associated extension parts respectively to or from the identified wound.

37. The combination of claim 30 wherein the at least first label provides indicia defining or pointing to instructions for applying or removing the first custom dressing part and its associated extension parts respectively to or from the identified wound.

38. The combination of claim 30 wherein said indicia points to a computer network site that provides instructions for applying and/or removing the first custom dressing part and its associated extension parts respectively to or from the identified wound.

39. The combination of claim 30 wherein the first packaging sheet includes a thermally printable-on layer and the at least first label is integrally formed as thermal printing on said thermally printable-on layer.

40. The combination of claim 30 and further comprising:
(f) a second label integrally formed on or attached to one of said first and second packaging sheets and providing additional indicia that performs at least one of the following functions:
indicating a route and/or method by way of which the first package and the first custom dressing part and one or more associated extension parts are to be delivered to the identified wound or patient having the identified wound, separately identifying the patient having the identified wound, indicating at least one of a prescribed date for application or prescribed date for removal of the first custom dressing part and one or more associated extension parts respectively to or from the identified wound, and defining or pointing to instructions for applying and/or removing the first custom dressing part and one or more associated extension parts respectively to or from the identified wound.

41. A method for coordinating packaging and delivery of a first customized multilayer wound dressing and of one or more dressing extension parts to a patient having a wound at a corresponding wound site for which the combination of the customized wound dressing and the one or more dressing extension parts are designed, the method comprising:

(a) automatically enclosing the customized wound dressing in a first sealed package;

(b) automatically enclosing the one or more of the dressing extension parts in a corresponding second or more sealed packages; and (c) automatically producing at least a first label that is attachable to or integrally formed on the first sealed package where the first label provides indicia that performs at least one of the following functions:

identifying the wound or wound site for which the combination of the customized wound dressing and the one or more extension parts are designed, separately identifying the patient having the identified wound or wound site, indicating a route and/or method and/or one or more persons by way of which said first and second or more packages and the correspondingly enclosed customized wound dressing and dressing extension parts are to be delivered to the identified wound or patient having the identified wound, indicating at least one of a prescribed date for application or prescribed date for removal of the customized wound dressing and its one or more extension parts respectively to or from the identified wound site, and defining or pointing to instructions for applying and/or removing the customized wound dressing and its one or more extension parts respectively to or from the identified wound site.

42. The method of claim 41 wherein said step of automatically enclosing the customized wound dressing includes:

depositing a base packaging sheet on an assembly stage;

forming two or more layers of the customized multilayer wound dressing and depositing them above the deposited base packaging sheet;

depositing a topside packaging sheet over the customized multilayer wound dressing; and bonding the deposited topside packaging sheet to the base packaging sheet.

43. The method of claim 41 wherein said step of automatically enclosing the customized wound dressing further includes:

automatically storing in a database, information regarding at least one of:

first information regarding applying or removing the customized dressing and its associated one or more extension parts respectively to or from the identified wound site;

second information regarding applying one or more prespecified liquids to the one or more extension parts or to prespecified liquid containment areas of the customized wound dressing prior to application;

third information regarding routing including that indicating how and/or into whose possession the packaged customized wound dressing and the associated extension parts are to be delivered prior to their application to the corresponding wound site;

fourth information regarding responsibility including identifying who is responsible for producing a corresponding wound image map and/or who is responsible for producing a corresponding wound zones characterizing data and/or who is responsible for producing a corresponding wound zone treatment plans or who is responsible for producing corresponding layer designs for respective layers of the customized multilayer wound dressing or who is responsible for specifying the one or more extension parts that are to be combined with the customized wound dressing.

44. A method of custom forming one or more fluid containment barriers in a given layer of a multilayer custom wound dressing that is associated with a pre-identified and pre-mapped wound for which the dressing is to be custom matched, where the custom wound dressing is further associated with one or more dressing extension parts that are to be operatively coupled to the custom wound dressing, the method comprising:

(a) providing a liquid impermeable first sheet material as defining one or more first layers of the multilayer custom wound dressing;

(b) defining through the first sheet material at least a first custom portal opening at a prespecified first location in the first sheet material, where the first custom portal opening is operatively mateable with at least a first of said one or more dressing extension parts so as to conduct a flow of liquid between the custom wound dressing and the first dressing extension part;

(c) providing a porous and hydrophilic second sheet material disposed over the first sheet material as defining one or more second layers of the multilayer custom wound dressing;

(d) depositing on the second sheet material and at a second location of the second sheet material corresponding both to a pre-mapped feature of the pre-identified wound and to the first custom portal opening defined at said prespecified first location in the first sheet material; a viscous liquid that can penetrate into and become embedded in the porous structure of the second sheet material such that after becoming so embedded the viscous liquid blocks or substantially inhibits one or more pre-defined other liquids or pre-defined gases or vapors from passing through the embedded viscous liquid; and (e) causing or allowing the deposited viscous liquid to become embedded in the second sheet material.

45. The method of claim 44 wherein:

said step of causing or allowing the deposited viscous liquid to become embedded includes picking an included material of the viscous liquid that has a viscosity after being embedded that substantially impedes the deposited viscous liquid from spreading in the second sheet material after becoming embedded therein.

46. The method of claim 44 wherein:

said step of causing or allowing the deposited viscous liquid to become embedded includes picking the included material of the viscous liquid to be a silicone with a viscosity in the range of 1 cSt to 10,000 cSt (CentiStokes).

47. The method of claim 46 wherein:
said picked silicone has a viscosity in the range of 100 cSt to 1,000 cSt.

48. The method of claim 44 wherein:
said step of causing or allowing the deposited viscous liquid to become embedded includes heating the deposited viscous liquid so as to thereby temporarily reduce its viscosity.

49. The method of claim 44 wherein:
said step of causing or allowing the deposited viscous liquid to become embedded includes depositing the viscous liquid as a mixture of a volatile solvent and one or more other dissolved liquids where viscosity of the one or more other dissolved liquids is reduced by the volatile solvent.

50. The method of claim 49 wherein:
said step of causing or allowing the deposited viscous liquid to become embedded further includes heating the deposited viscous liquid to a predetermined temperature above room temperature and at a predetermined time after the mixture of the volatile solvent and the one or more other dissolved liquids is deposited so to thereby hasten removal of the volatile solvent.

51. The method of claim 44 wherein said embedded viscous liquid defines one or more fluid containment barriers in the second sheet material and where a first of the one or more fluid containment barriers is positioned to block skinharming liquids from traveling laterally through the hydrophilic second sheet material to reach skin adjacent to the pre-identified and pre-mapped wound.

52. The method of claim 51 wherein a second of the one or more fluid containment barriers is positioned to separate an exudate absorbing region of the hydrophilic second sheet material from a moisture supplying region of the hydrophilic second sheet material.

53. The method of claim 44 wherein:
(b.1) said defining of the at least first custom portal opening at the prespecified first location in the first sheet material includes forming parallel slits through the first sheet material.

54. The method of claim 44 wherein:
(b.1) said defining of the at least first custom portal opening at the prespecified first location in the first sheet material includes forming one or more holes through the first sheet material.

55. The method of claim 44 wherein:
(b.1) said defining of the at least first custom portal opening at the prespecified first location in the first sheet material includes cutting out an area of prespecified shape and dimensions from the first sheet material.

56. The method of claim 44 wherein:
(b.1) said defining of the at least first custom portal opening at the prespecified first location in the first sheet material is accompanied by a further defining of at least a second custom portal opening at a prespecified second and different location in the first sheet material.

* * * * *